(12) United States Patent
Somasundaram et al.

(10) Patent No.: US 8,618,798 B2
(45) Date of Patent: Dec. 31, 2013

(54) ENHANCING SIGNALS

(75) Inventors: Samuel Somasundaram, Bookham (GB); Andreas Jakobsson, Sodra Sandby (SE); Michael Rowe, London (GB); John Smith, London (GB); Naveed Razzaq Butt, Lund (SE); Erik Gudmundson, Stockholm (SE); Kaspar Althoefer, London (GB)

(73) Assignee: King's College London, London (GB)

( * ) Notice: Subject to any disclaimer, the term of this patent is extended or adjusted under 35 U.S.C. 154(b) by 496 days.

(21) Appl. No.: 12/935,202

(22) PCT Filed: Mar. 27, 2009

(86) PCT No.: PCT/GB2009/000803
§ 371 (c)(1),
(2), (4) Date: May 16, 2011

(87) PCT Pub. No.: WO2009/118530
PCT Pub. Date: Oct. 1, 2009

(65) Prior Publication Data
US 2011/0210728 A1    Sep. 1, 2011

(30) Foreign Application Priority Data

Mar. 28, 2008 (GB) .................................. 0805688.9

(51) Int. Cl.
*G01V 3/00* (2006.01)
(52) U.S. Cl.
USPC .......................................... 324/307; 324/309
(58) Field of Classification Search
USPC ............................ 324/300–322; 600/407–445
See application file for complete search history.

(56) References Cited

U.S. PATENT DOCUMENTS 8,312,771 B2 * 11/2012 Randall et al. .................. 73/627
2008/0110263 A1 * 5/2008 Klessel et al. .................. 73/602

FOREIGN PATENT DOCUMENTS

EP         0 967 490 A2    12/1999
WO         WO-96/26453      8/1996

OTHER PUBLICATIONS

"International Application No. PCT/GB2009/000803, International Search Report mailed Jul. 15, 2009", 7 pgs.
"International Application No. PCT/GB2009/000803, Written Opinion of the International Searching Authority mailed Jul. 15, 2009", 14 pgs.
Behrens, Richard T., et al., "Signal Processing Applications of Oblique Projection Operators", IEEE Transactions on Signal Processing USA, vol. 42, No. 6, (Jun. 1994), 1413-1424.
Hoch, Jeffrey C., et al., "NMR Data Processing", XP002535033, Wiley-Liss, New York, (1996), 77-101.
Liao, Ming-Yuan, et al., "Noise excitation of half-integer quadrupolar spins at high field", Chemical Physics Letters, vol. 242, (Aug. 11, 1995), 89-94.
Scharf, L. L., et al., "Matched Subspace Detectors", IEEE Transactions on Signal Processing, vol. 42, No. 8, (Aug. 1994), 2146-2157.

(Continued)

*Primary Examiner* — Brij Shrivastav
(74) *Attorney, Agent, or Firm* — Schwegman Lundberg & Woessner, P.A.

(57) ABSTRACT

A method of testing a sample comprising the steps of: applying an excitation to the sample; detecting a response signal from the sample; processing a first part and a second part of the response signal; and determining from the second part of the response signal information with which to enhance the first part of the response signal.

52 Claims, 7 Drawing Sheets

(56) References Cited

OTHER PUBLICATIONS

Somasundaram, S. D., et al., "Detecting Stochastic Nuclear Quadrupole Resonance Signals in the Presence of Strong Radio Frequency Interference", Acoustics, Speech and Signal Processing, ICASSP 2008, IEEE International Conference ON, (Mar. 31, 2008), 3645-3648.

Somasundaram, S. D., et al., "Detection of Stochastic Nuclear Quadrupole Resonance Signals", Digital Signal Processing, 2007 15th International Conference ON, IEEE, (Jul. 1, 2007), 367-370.

Somasundaram, Samuel D., et al., "Countering Radio Frequency Interferene in Single-Sensor Quadrupole Resonance", IEEE Geoscience and Remote Sensing Letters IEEE USA, vol. 6, No. 1, (Jan. 2009), 62-66.

Somasundaram, Samuel D., et al., "Robust Detection of Stochastic Nuclear Quadrupole Resonance Signals", IEEE Transactions on Signal Processing, 2008 IEEE, vol. 56, No. 9, (2008), 4221-4229.

Somasundaram, Samuel D., et al., "Robust Nuclear Quadrupole Resonance Signal Detection Allowing for Amplitude Uncertainties", IEEE Transactions on Signal Processing, IEEE Service Center, Vo. 56, No. 3, (Mar. 1, 2008), 887-894.

Yang, D.-K., et al., "Suppression of ring-down in noise spectroscopy", Journal of Magnetic Resonance, vol. 158, No. 1-2, (Sep. 1, 2002), 73-78.

\* cited by examiner

| $k$ | 1 | 2 | 3 | 4 | 5 |
|---|---|---|---|---|---|
| $\omega_k$ | 1.9567 | 0.6214 | 0.1183 | -0.0724 | -0.7690 |
| $\beta_k$ | 0.0401 | 0.0128 | 0.0122 | 0.0192 | 0.0207 |
| $|\kappa_k|$ | 0.46 | 0.25 | 0.56 | 1.00 | 0.80 |
| $\angle \kappa_k$ (rads) | -0.1664 | 2.5218 | -2.7135 | -2.2918 | -0.7020 |

ENHANCING SIGNALS

PRIORITY CLAIM TO RELATED APPLICATIONS

This application is a national stage application under 35 U.S.C. §371 of PCT/GB2009/000803, filed Mar. 27, 2009, and published as WO 2009/118530 A1 on Oct. 1, 2009, which claims priority to Great Britian Application No. 0805688.9, filed Mar. 28, 2008, which applications and publication are incorporated herein by reference and made a part hereof in their entirety, and the benefit of priority of each of which is claimed herein.

The present invention relates to the detection of species by Nuclear Quadrupole Resonance (NQR). In particular, there are described methods of exploiting signal of interest (SOI) free samples in single-sensor spectroscopic methods, to reduce the influence of corrupting signals. SOI-free samples are samples not containing the SOI (e.g. the NQR signal), but only corrupting signals, such as interference (e.g. RF interference), spurious signals (e.g. signals excited using the excitation itself, including signals related to ferromagnetic and piezoelectric effects), and high-rank noise (e.g., thermal noise).

Nuclear quadrupole resonance (NQR) is a solid-state radio frequency (RF) spectroscopic technique that can be used to detect the presence of quadrupolar nuclei, such as the $^{14}$N nucleus prevalent in many explosives and narcotics. The practical use of NQR is restricted by the inherently low signal-to-noise ratio (SNR) of the observed signals, a problem that is further exacerbated by the presence of strong RF interference (RFI). In many NQR applications, RF interference (RFI) can be a major concern; for example, in the detection of landmines containing TNT, the relatively weak NQR signal is significantly affected by radio transmissions in the AM radio band. Often, extra RFI mitigation needs to be employed, be it passive methods which use specially designed antennas to cancel far-field RFI, or active methods which require extra antennae to measure the background RFI.

The present invention aims to provide a method of reducing the effects of this interference and/or other 'corrupting' signals. Methods applicable to conventional NQR and stochastic NQR are described. These methods may also find application in other forms of noise spectroscopy, such as stochastic NMR (nuclear magnetic resonance) and EPR (electron paramagnetic resonance), and in other forms of conventional spectroscopy, e.g., NMR and EPR.

International Patent Application No. PCT/GB96/00422 in the name of British Technology Group, and incorporated herein by reference, describes a method of nuclear quadrupole resonance testing a sample comprising a first type substance containing quadrupolar nuclei and a second type substance which may give rise to spurious signals which interfere with response signals from the quadrupolar nuclei, comprises applying a pulse sequence to the sample to excite nuclear quadrupole resonance, the pulse sequence comprising at least one pair of pulses; detecting response signals; and comparing, for the or each such pair, the respective response signals following the two member pulses of the pair; the pulse sequence being such that the respective spurious signals following the two member pulses can be at least partially cancelled by the comparison without the corresponding true quadrupole resonance signals being completely cancelled; and for the or each such pair, the two member pulses being of like phase.

Further information may be found in the following documents, which are herein incorporated by reference:

"Signal Processing Applications of Oblique Projection Operators," by R. T. Behrens and L. L. Scharf, *IEEE Transactions on Signal Processing*, vol. 42, no. 6, pp. 1413-1424, June 1994

"Matched Subspace Detectors," by L. L. Scharf and B. Friedlander, *IEEE Transactions on Signal Processing*, vol. 42, no. 8, pp. 2146-2157, August 1994.

Also incorporated herein by reference are the following papers by some of the inventors—as are the references contained therein—which are also referred to below:

Papers A

"Robust Detection of Stochastic Nuclear Quadrupole Resonance Signals," by S. D. Somasundaram, A. Jakobsson, M. D. Rowe, J. A. S. Smith, N. R. Butt and K. Althoefer, *IEEE Trans. On Signal Processing*, vol. 56, no. 9, pp. 4221-4229, September 2008.

"Countering Radio Frequency Interference in Single-Sensor Quadrupole Resonance," by S. D. Somasundaram, A. Jakobsson and N. R. Butt, *IEEE Geoscience and Remote Sensing Letters*, vol. 6, no. 1, pp. 62-66, January 2009.

Paper B

"Robust Nuclear Quadrupole Resonance Signal Detection Allowing for Amplitude Uncertainties," by S. D. Somasundaram, A. Jakobsson, and E. Gudmundson, *IEEE Trans. On Signal Processing*, vol. 56, no. 3, pp. 887-894, March 2008.

According to a first aspect of the invention, there is provided a method of testing a sample comprising the steps of:

applying excitation to the sample;

detecting a response signal from the sample;

processing a first part and a second part of the response signal; and determining from the second part of the response signal information with which to enhance the first part of the response signal.

As used herein, the term "response signal" includes a signal detected directly as a result of the excitation and a signal which has been processed subsequent to its initial detection. Hence, for example, "response signal" includes that obtained in stochastic techniques, wherein the response characteristic is reconstructed from the individual responses to a series of small excitations.

The method may be used to detect the NQR response from the $^{14}$N nucleus as found, for example, in explosives such as TNT or in narcotics such as cocaine and to all other quadrupolar nuclei, such as $^{35}$Cl in pharmaceutical analysis, $^{27}$Al in clay and other minerals, and $^{75}$As in toxic waste in abandoned land-fill. The method may also be used to detect the presence of a particular species within the sample. The method may also be used, for example, to distinguish between real and counterfeit medicines and to check on shelf life.

The applied excitation may be a radio-frequency excitation. Preferably, this excites a nuclear quadrupole resonance (NQR) response in the sample. Alternatively, the excitation may excite nuclear magnetic resonance or alternatively electron paramagnetic resonance in the sample.

The excitation may be conventional spin-echo or pulse-sequence excitation (for NQR, this is termed cNQR).

Alternatively, the excitation may be stochastic or noise excitation (for NQR, this is termed sNQR). Preferably, the stochastic excitation is random or pseudo-random, and the signal-of-interest (SOI) is obtained by cross-correlating the (raw) excitation signal with the time-domain response signal to produce a correlation-domain response signal. This correlation-domain response signal may be analogous to the free-induction decay (FID) signal obtained in cNQR.

Stochastic NQR (sNQR) has the advantage over conventional NQR (cNQR) in that substantially lower power excitation can be used, allowing for safer, more portable operation, and that data can be essentially collected continuously (in cNQR, the data collection rate is slowed and therefore detection time lengthened by samples with large spin-lattice relaxation times).

Preferably, for sNQR, the response signal is sampled (i.e. data collected) using multiple-point acquisition i.e. by taking multiple samples between consecutive excitation pulses. Preferably, unlike in the prior art, algorithms are used to estimate spectral parameters directly from the resulting correlation-domain signal. This has the advantage, unlike in the prior art, that it is not necessary to perform repeat measurements in order to construct a complete gap-less correlation-domain signal i.e. data can (essentially) be acquired continuously.

In any embodiment, the first part of the response signal may comprise a signal of interest (SOI) and 'corrupting' signal such as an interference signal and/or noise; the second part of the response signal may comprise substantially or solely a corrupting signal such as an interference signal and/or noise. Typically the corrupting signal is of the same type in the first and second parts.

The 'corrupting' signal may be interference, such as radio-frequency interference, spurious signals or high-rank or thermal noise.

Preferably, the SOI is relatively strong, or non-negligible, in the first part of the response signal and relatively weak, or substantially negligible, in the second part of the response signal. Between the first and second parts of the response signal may be an intermediate region of the response signal wherein the SOI is either strong or non-negligible. Preferably this intermediate region of the response signal is not used in the processing step and/or is not detected.

Preferably, the start of the first part of the response signal is at a period after the ringdown time of the sample, as known or measured a priori.

Alternatively, and preferably in the case of sNQR, ringdown effects may be suppressed by means of Q-damping circuitry, phase cycling and the technique of composite pulses.

Preferably, the end of the first part of the response signal is at a period after the associated excitation (for example, excitation pulse) which is less than five times, preferably less than three times, more preferably less than twice, and yet more preferably less than the longest spin-phase decay time ($T_{2,max}^*$) of the sample. The value of $T_{2,max}^*$ is known or can be measured a priori.

It will be understood that the concept of a time axis as used in describing the signals and responses of conventional NQR (cNQR) in the time domain is analogous to a cross-correlation lag axis as used in stochastic NQR (sNQR) in the cross-correlation domain, and that the use of 'time' (including the quantity $T_{2,max}^*$) in the sNQR context may be understood to refer to a degree of evolution of the response signal.

It is to be understood that wherever the term $T_{2,max}^*$ is used, it is interchangeable with the more familiar term in the art $T_{2,max}^*$.

Preferably, the start of the second part of the response signal is at a period after the associated excitation which is more than at least one, two, three or five times the longest spin-phase decay time ($T_{2,max}^*$) of the sample. Preferably, the start of the second part of the response signal is at a period by which the FID has decayed to such an extent that there is essentially no SOI present in the second part of the response signal.

Preferably, the start of the second part is at a period after the start of the first part that is more than 1, 2, 3, or 5 times the duration of the first part.

Preferably, the method further comprises processing the second part of the response signal in order to obtain a model of the corrupting signal. Preferably, the model of the corrupting signal is used to reduce the effects of the corrupting signal in the first part of the response signal.

Preferably, for stochastic NQR (sNQR), the resulting correlation-domain signal is modelled as a gapped free-induction decay (FID). Algorithms may be used to estimate the required parameters directly from the 'gapped' data.

The corrupting signal may be modelled as belonging to a low-rank linear subspace, embedded in wideband noise, and the second part of the response signal may be used to make an estimate of this low-rank linear subspace, and may be used in reducing the influence of the corrupting signal in the part of the response signal containing the SOI.

Alternatively, the corrupting signal may be modelled as pure zero mean Gaussian noise, and the second part of the response signal may be used to estimate the corresponding noise covariance matrix and thus allow the construction of a pre-whitening transform for use in reducing the influence of the corruptive signal in the part of the response signal containing the SOI.

Preferably, other parts of the response signal may also be modelled, including, for example the first part of the response signal, which is to say the SOI with the corrupting signal.

Preferably, the model of the corrupting signal may be used to adjust the model of the first part of the response signal.

Preferably, spurious signals are reduced by repeating the excitation at cycled phases, for example as taught in International Patent Application No. PCT/GB96/00422.

Preferably, only a single sensor is used. That is, the design is preferably non-gradiometric.

The invention also provides apparatus with which to put into effect the methods of the present invention. Preferably, this consists of a transmitter, with which to excite the sample, and a receiver with which to detect the response signal. Transmitting and receiving functions may be combined. Preferably, the transmitter comprises an RF source, pulse modulator, an RF power amplifier, and a probe. The probe may consist of a shield, an RF antenna and tuning electronics.

A processor, associated memory and storage may also be provided.

The invention also provides a computer program and a computer program product for carrying out any of the methods described herein and/or for embodying any of the apparatus features described herein, and a computer readable medium having stored thereon a program for carrying out any of the methods described herein and/or for embodying any of the apparatus features described herein.

The invention also provides a signal embodying a computer program for carrying out any of the methods described herein and/or for embodying any of the apparatus features described herein, a method of transmitting such a signal, and a computer product having an operating system which supports a computer program for carrying out any of the methods described herein and/or for embodying any of the apparatus features described herein.

The invention extends to methods and/or apparatus substantially as herein described with reference to the accompanying drawings.

Any feature in one aspect of the invention may be applied to other aspects of the invention, in any appropriate combination. In particular, method aspects may be applied to apparatus aspects, and vice versa.

Furthermore, features implemented in hardware may generally be implemented in software, and vice versa. Any reference to software and hardware features herein should be construed accordingly.

It will be understood that the present invention as described below is purely by way of example; modifications of detail can be made within the scope of the invention.

These and other aspects of the present invention will become apparent from the following exemplary embodiments that are described with reference to the accompanying figures in which.

Figure 1:
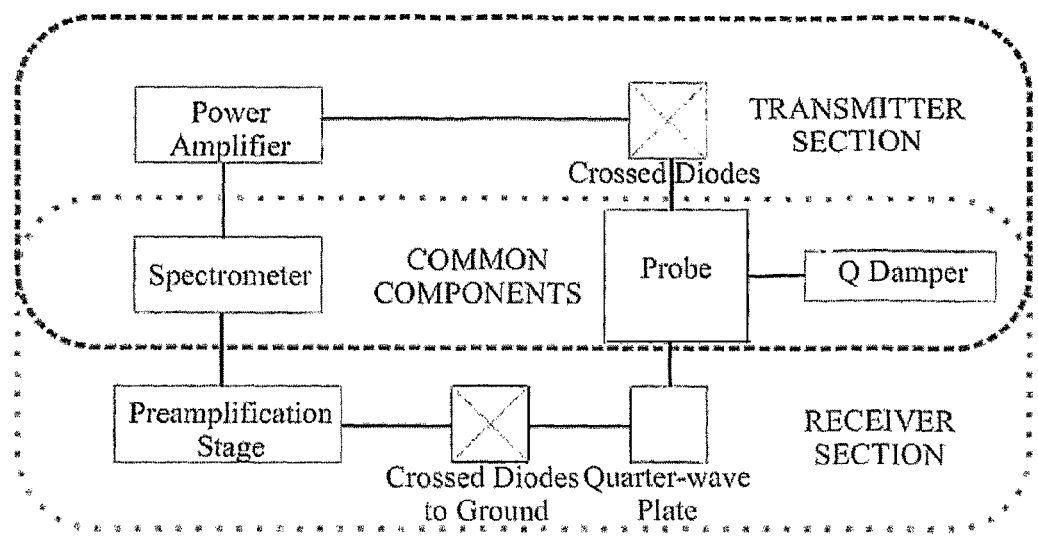
FIG. 1 is a block diagram of an NQR system.

FIG. 1 illustrates a typical NQR system. There are two main sections: the transmitter section, used to excite the sample with the desired radio-frequency (RF); and a receiver section, used to detect the weak RF signals generated by the quadrupolar nuclei. The heart of the apparatus is the spectrometer, which performs both transmitter and receiver functions. Given a pulse sequence, the spectrometer, which contains an RF source and pulse modulation hardware, will produce RF pulses with the desired characteristics, ready for amplification by the RF power amplifier. The amplified pulse sequence is then transmitted to the sample via the probe. The probe consists of a shield, an RF antenna and the electronics required to tune the antenna to the correct excitation frequency and match its impedance to the other electronic devices. In one embodiment, in order to develop and test many of the algorithms, it was necessary to obtain data without external RFI. Therefore, a shield big enough to house the coil and the tuning and matching circuitry, with an easily removable lid, is provided. The shield is not a Faraday shield, as it only shields the contents from electric fields and not magnetic fields.

Figure 2:
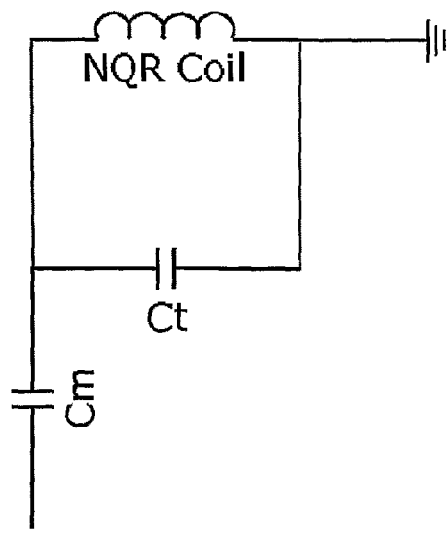
FIG. 2 is a schematic diagram of the tuning and matching circuitry.

FIG. 2 shows the schematic diagram of the circuitry needed to tune the RF antenna to the excitation frequency, and match the impedance of the probe to the rest of the hardware. It is noted that variable capacitors were used for both tuning, Ct, and matching, Cm. The total capacitance (Cm+Ct) needed to tune the probe to a given frequency is given by $$C = \frac{1}{4\pi^2 f^2 L},$$

where f and L denote the excitation frequency and the coil/antenna inductance, respectively. Often, the outputs of power amplifiers are quite noisy, therefore crossed diodes are provided to isolate the output of the power amplifier from the probe whenever pulses are not being transmitted. A crossed-diode is a nonlinear element because it looks like a good conductor for large incoming signals, but like a poor conductor to signals of either polarity. Therefore, putting crossed-diodes between the power amplifier and the probe means that the high power RF pulses are passed successfully to the probe, but at all other times the probe is isolated from the transmitter section and therefore also from any noise in the transmitter section.

The receiver section consists of the RF antenna to measure the weak signals from the sample, a pre-amplification stage to enhance the weak signal, and hardware (within the spectrometer) used to demodulate the measured signal at the excitation frequency. A single antenna is provided for both transmit and receive. Since the transmitted RF pulses are several orders of magnitude greater than the received NQR signals, extra electronic circuitry is required in order to protect the sensitive receiver section during the RF pulse. The crossed-diodes to ground protect the sensitive receiver circuitry during an RF pulse, since during a pulse the cross-diodes act as a good conductor "shunting" the signal to ground. When the signal falls below the diode threshold voltage, the signal is passed to the rest of the receiver circuit. The shorted quarter wave cable, between the probe and the rest of the receiver section, performs a kind of band pass filtering operation. It acts as an open circuit only for signals around the design frequency and will attenuate all others, thus helping to filter out unwanted noise.

Quality (Q) Factors and Q Damping

The Quality (Q) factor is a measure of the quality of a resonant system and is important, firstly, as the SNR is proportional to $Q^{1/2}$, secondly, because the recovery time of the tuned circuit is proportional to the Q, and thirdly, because the bandwidth of the system is effected by it. In a tuned RF receiver circuit, the Q is defined as $$Q = \frac{1}{R}\sqrt{\frac{L}{C}},$$

where R is the resistance in Ohms, L is the inductance in Henries and C is the capacitance in Farads. Noting that if the angular frequency ω is given by $$\omega = \frac{1}{\sqrt{LC}},$$

the Q may be expressed as $$Q = \frac{\omega L}{R}.$$

A useful expression for measuring the Q of a tuned circuit is $$Q = \frac{f_0}{f_h - f_l} \triangleq \frac{f_0}{\Delta f},$$

where $f_0$ is the centre frequency, $f_h$ is the upper cut-off frequency and $f_l$ is the lower cut-off frequency. The lower/upper cut-off frequency is defined as the frequency below/above which the output of the tuned circuit is reduced to 70.7% of the reference voltage at f_0.

NQR signals can generally not be measured during or directly after the excitation pulses, as these pulses are many orders of magnitude greater in amplitude than the generated NQR signals, leading to a dead-time between the centre of the excitation pulse and the first sample. Rapid detection of signals that decay quickly in the time domain (and are broad in the frequency domain) is limited by the length of this dead-time, as the strongest part of the signal will have been lost in this time. The biggest contributor to this dead-time is the time required for the RF voltage, due to the excitation, to decay (or ring-down) to levels of the same order of magnitude as the NOR signals. The ring-down time is proportional to the Quality (Q) factor of the probe, so one possible option would be to lower the Q-factor of the probe; however, the SNR is proportional to $Q^{1/2}$. Therefore, ideally one would like to lower the Q of the probe directly after the transmit pulse, in order to allow rapid ring-down of the residual transmit RF, then increase the Q when the NQR signal is sampled, in order to give a high SNR. The task of the Q damper is to allow rapid switching of the Q of the receiver circuit, as required.

Figure 3:
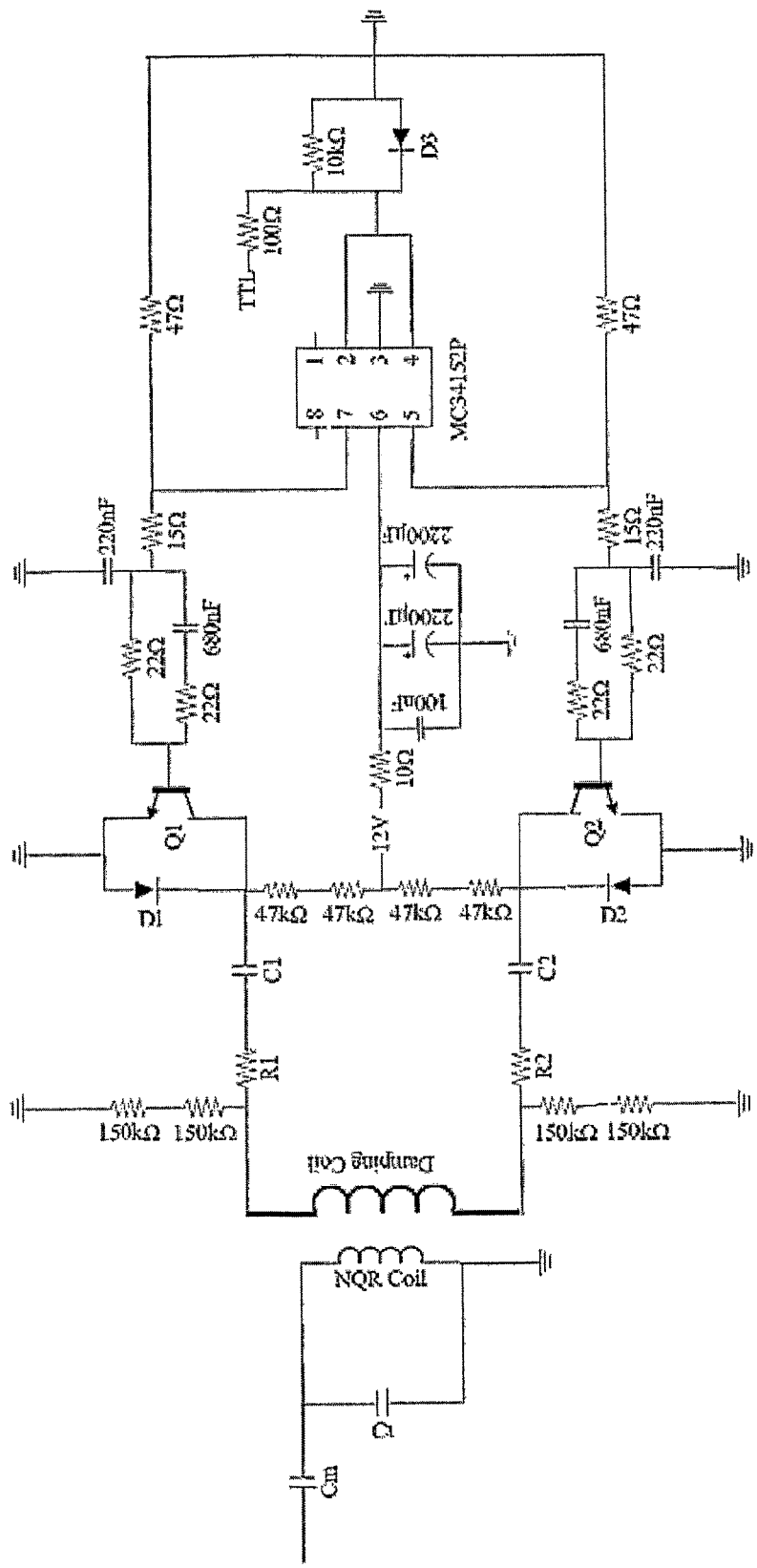
FIG. 3 is a circuit diagram of the Q-damper.

FIG. 3 shows the circuit diagram of the Q-damper. It is noted that the values of the components R1, R2, C1 and C2 depend upon the specifications of the damping coil and the operating frequency. Further, Q1 and Q2 are BUP35 NPN transistors, D1 and D2 are STTA806D diodes, D3 is a BZX86C6V2 diode and MC34152P is a MOSFET Driver integrated circuit.

First Embodiment
Robust Detection of Stochastic Nuclear Quadrupole Resonance Signals This embodiment describes how, in noise spectroscopy, SOI-free correlation domain samples can be used to reduce the influence of corruptive signals. This is further discussed in Papers A.

In stochastic/noise spectroscopy, the SOI is obtained by cross-correlating the (pseudo white) noise excitation sequence with the time domain response, yielding the correlation domain signal. Often, however, only a very small portion of the correlation domain signal will contain the SOI; therefore, the rest of the signal can be considered SOI-free.

Two examples of exploiting SOI-free samples in stochastic NQR are described. In one example it is assumed that the corrupting signals comprise of interference, belonging to a low rank linear subspace, embedded in white Gaussian noise. An estimate of the low rank linear subspace is formed from the signal-of-interest free samples and used to reduce the influence of the corruptive signals; the resulting algorithm is termed SEAQUER. In the second example, the corruptive signal is assumed to be pure zero mean Gaussian noise. An estimate of the noise covariance matrix is formed from the signal-of-interest free samples, from which a prewhitening transform, which can be used to reduce the influence of the corruptive signals, is derived; the resulting algorithm is termed RCDAML.

This invention and the SEAQUER and RCDAML techniques are applicable to all forms of noise spectroscopy. Note that SEAQUER and RCDAML are examples of two ways of exploiting the SOI-free samples to reduce the influence of corrupting signals.

Nuclear quadrupole resonance (NQR) is a solid-state radio frequency (RF) spectroscopic technique, allowing the detection of compounds containing quadrupolar nuclei, a requirement fulfilled by many high explosives and narcotics. The practical use of NQR is restricted by the inherently low signal-to-noise ratio of the observed signals, a problem that is further exacerbated by the presence of strong RF interference (RFI). The current literature focuses on the use of conventional, multiple-pulsed NQR (cNQR) to obtain signals. An alternative method called stochastic NQR (sNQR) is provided, having many advantages over cNQR, one of which is the availability of signal-of-interest free samples. In this embodiment, these samples are exploited forming a matched subspace-type detector and a detector employing a pre-whitening approach, both of which are able to efficiently reduce the influence of RFI. Further, many of the ideas already developed for cNQR, including providing robustness to uncertainties in the assumed complex amplitudes and exploiting the temperature dependencies of the NQR spectral components, are recast for sNQR. The presented detectors are evaluated on both simulated and measured trinitrotoluene (TNT) data.

I-1. Introduction

Nuclear quadrupole resonance (NQR) is a solid-state radio frequency (RF) technique that can be used to detect the presence of quadrupolar nuclei, such as the $^{14}$N nucleus prevalent in many explosives and narcotics. Historically, the linear response of the NQR system known as the free induction decay (FID) was measured, using a simple one-pulse experiment; however, since the advent of multiple-pulse techniques, the trend has instead been to obtain nonlinear responses, enabling signals with higher signal-to-noise ratios (SNRs) to be obtained in a shorter time. The aforementioned acquisition methods, which are termed collectively as conventional NQR (cNQR) methods, use powerful coherent RF modulated pulses to interrogate the sample. An alternative method for acquiring NQR signals, called stochastic NQR (sNQR), uses stochastic (or noise) excitation. Whilst stochastic excitation was proposed for nuclear magnetic resonance (NMR) as early as 1970, there are still relatively few publications on stochastic NMR.

In sNQR, trains of low power coherent pulses, whose phases or amplitudes are randomized, are used to interrogate the sample; herein, such pulses are termed stochastic pulses. Providing sufficiently weak stochastic pulses are used, the NQR system maybe treated as linear and time invariant. Thus, cross-correlation of the observed time domain signal with a white input sequence yields the linear response (or FID) which may be well modelled as a sum of exponentially damped complex sinusoids.

An important advantage of sNQR, as compared to cNQR, is that significantly lower RF powers are required to achieve the same excitation bandwidth, which may be beneficial, for instance, in the area of humanitarian de-mining where lightweight, man-portable and battery-operated detectors are required, or for interrogating samples hidden on people, where there are strict limits on the amount of RF power that may be used.

Furthermore, sNQR has an immediate advantage over cNQR when investigating compounds with long spin-lattice relaxation times, such as trinitrotoluene (TNT). In cNQR, a restrictive delay, usually five times the spin-lattice relaxation time, must be adhered to in between measurements, resulting in unfeasibly long detection times. This problem is alleviated in sNQR and data can (essentially) be acquired continuously.

It is noted that although broadband excitation has been shown to be achievable for sNQR, a limitation of previous work is that the bandwidth of the received signal is limited by the time between consecutive stochastic pulses, here termed the stochastic dwell time; for example, the bandwidth of the received signal is limited to, say, 25 kHz. This as previous techniques acquired only a single data point between consecutive stochastic pulses, a technique here termed as single-point acquisition, and therefore the sampling period is equal to the stochastic dwell time. Due to effects such as ringdown, there is a limit on how short one can make the stochastic dwell time (and thus also the sampling period when single-point acquisition is used). It has been shown, for both NMR and electron paramagnetic resonance (EPR), that the spectral bandwidth can be increased by acquiring two or more data points between consecutive pulses. Herein, such a technique is employed for sNQR, here termed as multiple-point acquisition. The resulting correlation domain signal can then be well modeled as an FID with periodically recurring gaps. In the prior art, for NMR, it is proposed to handle these gaps by repeating the measurements with differing experimental settings so that the gaps occur in different places, and then stitching the resulting gapped FIDs together to form a single seamless FID. Rather, algorithms are provided that are able to estimate the required spectral parameters directly from the gapped data.

In many NQR applications, RF interference (RFI) can be a major concern; e.g., in the detection of landmines containing TNT, the relatively weak NQR signal is significantly affected by radio transmissions in the AM radio band. In cNQR, extra RFI mitigation often needs to be employed, be it passive methods which use specially designed antennas to cancel far-field RFI, or active methods which require extra antennae to measure the background RFI. For sNQR, however, it is possible to cancel the effects of the RFI without the need for these additional techniques. It is noted that the FID will have decayed to negligible levels after five times the longest spin-phase memory decay time, here denoted $T_{2,max}^*$, which can be measured a priori. It is noted that the spin-phase memory decay time of a resonant line can vary between samples, due to differing sample crystallinity and/or the presence of impurities. The spin-phase memory decay time is upper bounded by the spin-spin relaxation time, which does not change between samples, and could be used instead. Therefore, only a relatively small subset of the correlation domain data will contain the sNQR signal; however, RFI components will likely be present throughout the entire correlation domain.

One alternative is to use the correlation domain samples known not to contain NQR components, here termed the signal-of-interest free samples, to obtain an estimate of the noise covariance matrix, and then use this to pre-whiten any unknown noise coloring; such an approach leads to the here proposed Robust Correlation Domain Approximate Maximum Likelihood (RCDAML) detector.

Another alternative is to assume that the RFI lies in a low-rank linear interference subspace that can be estimated from the signal-of-interest free samples. The interference subspace is then exploited to form a matched subspace-type detector. This approach yields the Subspace-based EvaluAtion of QUadrupole resonance signals Exploiting Robust methods (SEAQUER) detector introduced in Section I-3.

Furthermore, we beneficially exploit the dependencies of the NQR frequencies on temperature when forming both the SEAQUER and RCDAML detectors. Additionally, it has been shown to be beneficial to exploit prior knowledge concerning the complex amplitudes of the NQR components, which allows such information to be exploited, but also allows for uncertainty in it. This is further discussed in Paper B.

The data model for the correlation domain sNQR signal is outlined in Section I-2. Sections I-3 and I-4 contain the derivations for the SEAQUER and RCDAML algorithms, respectively. In Section I-5, the performances of the proposed detectors are evaluated. Finally, Section I-6 draws some conclusions.

I-2. Data Model

If the sample is interrogated with a stochastic excitation sequence consisting of P stochastic pulses, and N samples are acquired after each pulse, then the observed time domain signal will contain NP samples. Cross-correlation of the time domain signal with the (white) exciting sequence, yields the correlation domain signal r(t), also consisting of NP samples, which may be well modelled as a gapped FID, consisting of evenly spaced blocks of data, sampled at the data dwell time, $D_w$. It is noted that if a pseudo random noise sequence such as the maximum length binary sequence (MLBS) is used for excitation, then the fast Hadamard transform can be used for cross-correlation. The p th correlation domain block may then be written as $$r^p(t) = \sum_{k=1}^{d} \alpha_k \xi_k^{t+pT_s} + w^p(t); \; p = 0, \ldots, P-1 \quad (1)$$

$$\xi_k = e^{i\omega_k(T) - \beta_k},$$

with $t = t_0, \ldots t_{N-1}$, $T_s$, d and T denoting the block sampling time (measured with respect to the centre of the stochastic pulse), the stochastic dwell time, the known number of FID components and the unknown temperature of the compound under investigation, respectively. Furthermore, $\alpha_k$, $\omega_k(T)$ and $\beta_k$ denote the complex amplitude, the frequency shifting function and the sinusoidal damping constant of the k th FID component, respectively. For many compounds, such as TNT, the frequency shifting functions, at likely temperatures of the compound, can be well modelled as $$\omega_k(T) = a_k - b_k T, \quad (2)$$

where $a_k$ and $b_k$, for k=1, d, are given constants. Finally, $w^p(t)$ denotes an additive coloured noise, due to thermal (Johnson) noise and external RFI, where it is here assumed that any known noise colouring has already been removed. This is further discussed in Paper B.

The maximum number of correlation blocks that should be used for estimation of the FID parameters are the first $\tilde{P}$ blocks that correspond to times less than or equal to $5T_{2,max}^*$. A subset of the remaining $P-\tilde{P}$ blocks, here selected as the last $\breve{P}$ blocks, can then be used for interference and noise rejection.

In the following, $(\cdot)^T$, $(\cdot)^*$, $(\cdot)^\dagger$, $\|\cdot\|_2$, $\text{Re}\{\cdot\}$ and $E\{\cdot\}$ denote the transpose, the Hermitian transpose, the Moore-Penrose pseudoinverse, the two-norm, the real operator and the expectation operator, respectively.

I-3. The SEAQUER Algorithm

Using (1), the p th data block may be expressed as $$r_N^p \triangleq [r^p(t_0) \; \ldots \; r^p(t_{N-1})]^T = A_\theta^p \alpha + w_N^p \quad (3)$$

where $w_N^p$ is defined similar to $r_N^p$, and $$A_\theta^p = \begin{bmatrix} \xi_1^{t_0+pT_s} & \cdots & \xi_d^{t_0+pT_s} \\ \vdots & \ddots & \vdots \\ \xi_1^{t_{N-1}+pT_s} & \cdots & \xi_d^{t_{N-1}+pT_s} \end{bmatrix} \quad (4)$$

$$\alpha = [\alpha_1 \; \alpha_d]^T,$$

with $\theta = [T\beta^T]^T$ and $\beta = [\beta_1 \; \beta_d]^T$ denoting the nonlinear parameter vector and the vector of unknown sinusoidal dampings, respectively. Thus, the data model for $\tilde{P}$ data blocks can be written as $$r_{N\tilde{P}} \triangleq [(r_N^0)^T \ldots (r_N^{\tilde{P}-1})^T]^T = H_{\bar{\theta}}\alpha + w_{N\tilde{P}} \qquad (5)$$

where $w_{N\tilde{P}}$ is defined similar to $r_{N\tilde{P}}$, and $$H_{\bar{\theta}} = [(A_{\bar{\theta}}^0)^T (A_{\bar{\theta}}^{\tilde{P}-1})^T]^T. \qquad (6)$$

I-3.1. Exploitation of the Interference Subspace

Here, it is further assumed that the coloured noise term, $w_{N\tilde{P}}$, may be factored as $$w_{N\tilde{P}} = S\phi + e_{N\tilde{P}}, \qquad (7)$$

with S, $\phi$ and $e_{N\tilde{P}}$ denoting the basis for the interference subspace, the interference subspace weights and an additive white Gaussian noise, respectively. Thus, (5) may be rewritten as $$r_{N\tilde{P}} = H_{\bar{\theta}}\alpha + S\phi + e_{N\tilde{P}}. \qquad (8)$$

It is noted that the interference subspace will typically be unknown, and therefore must be estimated from the available data. Such an estimate may be formed by using the $\check{P}$ end correlation domain data blocks, by first constructing a $N\tilde{P} \times (\check{P}/\tilde{P})$ data matrix, $\check{X}$, in which each column consists of $\tilde{P}$ end correlation domain data blocks. Thus, $\check{P}$ is selected as an integer multiple of $\tilde{P}$. The data matrix is then factorized using the singular value decomposition (SVD), i.e., $\check{X} = \check{U}\check{U}_{\check{V}^*}$, where $\in R^{N\tilde{P} \times \check{P}/\tilde{P}}$ is a diagonal matrix with the singular values arranged in nonincreasing order on its main diagonal, and where $\check{U} \in C^{N\tilde{P} \times N\tilde{P}}$ and $\check{V} \in C^{\check{P}/\tilde{P} \times \check{P}/\tilde{P}}$ are unitary matrices containing the left and right singular vectors, respectively. The $d_{int}$ dominant left singular vectors may then be used as an estimate of the basis for the interference subspace, $\hat{S} \in C^{N\tilde{P} \times d_{int}}$, i.e., $$\hat{S} = [\check{u}_1 \ldots \check{u}_{d_{int}}] \qquad (9)$$

where $\check{u}_k$ denotes the k th left singular vector of $\check{X}$. If the interference consists of a mixture of either sinusoids or damped sinusoids, then the best choice for $d_{int}$ is as the number of sinusoidal components. If no prior knowledge of the number of RFI components is available, then a reasonable estimate may be obtained by examining the singular values of $\check{X}$. Here, using a minimum description length (MDL) like rule to select the rank of the interference subspace is proposed, forming $$MDL(k) = N\log(\sigma_k) + k\log(N) \qquad (10)$$
$$d_{int} = \arg\min_k \{MDL(k)\},$$

where $\sigma_k$ is the k th singular value of the data matrix. It is remarked that a proper MDL test could also be formed, but note that the rule suggested in (10) does not require any knowledge of the probability density function (PDF) and offers a fast and often adequate estimate of the model order. Given the estimate for the interference subspace, $\hat{S}$, which for notational convenience is herein simply refer to as S, the maximum likelihood estimate of is given by $$\theta = [\bar{\theta}^T \alpha^T \phi^T]^T, \qquad (11)$$

$$\hat{\theta} = \arg\min_{\theta} \|H_{\bar{\theta}}\alpha + S\phi - r_{N\tilde{P}}\|_2^2. \qquad (12)$$

Minimizing (12) with respect to $\phi$ yields an estimate of $\phi$ as $$\hat{\phi} = S^\dagger(r_{N\tilde{P}} - H_{\bar{\theta}}\alpha), \qquad (13)$$

where it is noted that $S^\dagger = S^*$ as S is a unitary matrix. Substituting (13) into (12) yields the compressed minimization $$\min_{\alpha,\bar{\theta}} \left\| \prod_S^\perp [H_{\bar{\theta}}\alpha - r_{N\tilde{P}}] \right\|_2^2, \qquad (14)$$

where $$\Pi_S^\perp = I - SS^\dagger. \qquad (15)$$

Thus, the data and model vectors are projected onto the space orthogonal to the interference subspace, nulling the effects of the interference.

I-3.2. Robust Complex Amplitude Estimation

To exploit the prior knowledge typically available for the complex amplitudes, $$\alpha = \rho\kappa, \qquad (16)$$

Is first factorized, where $\rho$ is the common (real-valued) magnitude scaling due to the signal power, and $\kappa$ is the (complex) amplitude vector, normalized such that its largest magnitude equals unity, containing both the phases and the relative magnitudes of the d complex amplitudes. This is further discussed in Paper B. It is here considered the case when the assumed (normalized) amplitude vector, here denoted $\bar{\kappa}$, as well as the actual (normalized) amplitude vector, $\kappa$, belong to an uncertainty hypersphere with radius $\sqrt{\epsilon}$, i.e., $$\|\kappa - \bar{\kappa}\|_2^2 \leq \epsilon. \qquad (17)$$

The choice of $\epsilon$ should reflect the uncertainty in the complex amplitudes, typically obtained as a result of the experimental setup. Herein, as further discussed in Paper B, $\epsilon$ is modelled as a random variable, $\underline{\epsilon}$, formed as $$\varepsilon = \|\kappa - \bar{\kappa}\|_2^2 = \sum_{k=1}^d |\kappa_k - \bar{\kappa}_k|^2, \qquad (18)$$

where $\kappa_k$ is modeled as $$\kappa_k = (|\bar{\kappa}_k| + \Delta_k^m)e^{i(\angle\bar{\kappa}_k + \Delta_k^p)}, \qquad (19)$$

with $|\bar{\kappa}_k|$ and $\angle\bar{\kappa}_k$ denoting the assumed magnitude and phase components; $\Delta_k^m$ and $\Delta_k^p$ are random variables denoting the errors in the magnitude and phase components. The magnitude errors, $\Delta_k^m$, are modelled as independent truncated Gaussian random variables, parameterized by the variance $\sigma_m^2$. The phase errors, $\Delta_k^p$, are assumed to be independent identically distributed random variables, uniformly distributed over the interval $[-P,P]$, where $0 \leq P \leq \pi$ is selected according to the uncertainty in the phases. The statistics of the amplitude errors should be obtained from real measurements.

By restricting the actual (normalized) amplitude vector to this hypersphere, an estimate of the vector best fitting the observed data can be obtained by solving the following constrained minimization $$\min_\kappa \left\| \prod_S^\perp [\rho H_{\bar{\theta}}\kappa - r_{N\tilde{P}}] \right\|_2^2 \text{ subject to } \|\kappa - \bar{\kappa}\|_2^2 \leq \varepsilon, \qquad (20)$$

where $\bar{\theta}$ is here assumed known. It is noted that an initial estimate of $\rho$ is needed to solve (20). By noting that $\rho$ is the largest magnitude in $\alpha$, an initial estimate of $\rho$ may be obtained as $$\hat{\rho} = \max\{|\hat{\alpha}_{LS}|\}, \quad (21)$$

with max $\{x\}$ denoting the maximum element in the vector x, and where $$\hat{\alpha}_{LS} = (\Pi_S^\perp H_{\bar{\theta}})^\dagger r_{N\tilde{P}} \quad (22)$$

is obtained by minimizing (14) with respect to $\alpha$. Using the SVD to factor $\Pi_S^\perp H_{\bar{\theta}} = U\Sigma V^*$ and using (21)-(22), the minimization in (20) can be rewritten as $$\min_{\tilde{\kappa}} \|\hat{\rho} \sum \tilde{\kappa} - \tilde{r}\|_2^2 \text{ subject to } \|V[\kappa - \tilde{\kappa}]\|_2^2 \le \varepsilon, \quad (23)$$

where $\tilde{r} = U^* \Pi_S^\perp r_{N\tilde{P}}$, $\tilde{\kappa} = V^*\kappa$ and $\tilde{\tilde{\kappa}} = V^*\bar{\kappa}$. If the unconstrained least squares solution of $\tilde{\kappa}$ is within the feasible region then it is a solution to (23); however, if this is not the case then the solution will occur on the boundary of the feasible region and is found from $$\min_{\tilde{\kappa}} \|\hat{\rho} \sum \tilde{\kappa} - \tilde{r}\|_2^2 \text{ subject to } \|V[\kappa - \tilde{\kappa}]\|_2^2 = \varepsilon, \quad (24)$$

which can be solved using the method of Lagrange multipliers. This is further discussed in Paper B. To ensure that $\rho$ and $\kappa$ are uniquely defined, the robust estimate of $\kappa$ is formed as $$\hat{\kappa} = \frac{V\tilde{\kappa}}{\max\{|V\tilde{\kappa}|\}}. \quad (25)$$

Given $\hat{\kappa}$, $\rho$ may be re-estimated as $$\hat{\rho} = Re\{(\Pi_S^\perp H_{\bar{\theta}}\hat{\kappa})^\dagger r_{N\tilde{P}}\}. \quad (26)$$

Forming $$\hat{\alpha} = \hat{\kappa}\hat{\rho}, \quad (27)$$

and substituting it into (14) yields the residual least squares error $$\varphi_{\bar{\theta}} = \|\Pi_S^\perp (H_{\bar{\theta}}\hat{\alpha}_{\bar{\theta}} - r_{N\tilde{P}})\|_2^2, \quad (28)$$

between the model and the observed data, where we have used the notation $\hat{\alpha}_{\bar{\theta}}$ to stress the dependence of $\hat{\alpha}$ on $\bar{\theta}$. In general, the nonlinear parameter vector, $\bar{\theta}$, will be unknown and must be estimated by minimizing $\varphi_{\bar{\theta}}$ over $\bar{\theta}$, using a grid search. Thus, for each value of $\bar{\theta}$, the residual error, $\varphi_{\bar{\theta}}$, is evaluated using (20)-(28). The estimated value of $\bar{\theta}$ is then found as the parameter vector minimizing this error, i.e., $$\hat{\bar{\theta}} = \arg\min_{\bar{\theta}} \varphi_{\bar{\theta}}. \quad (29)$$

The test statistic is formed as an (approximate) generalized likelihood ratio (GLRT) detector, i.e.

$$T(r_{N\tilde{P}}, \hat{\alpha}_{\hat{\bar{\theta}}}) = \frac{r_{N\tilde{P}}^* \Pi_S^\perp r_{N\tilde{P}}}{\|\Pi_S^\perp (r_{N\tilde{P}} - H_{\hat{\bar{\theta}}}\hat{\alpha}_{\hat{\bar{\theta}}})\|_2^2}, \quad (30)$$

where the signal component is deemed present if and only if $T(r_{N\tilde{P}}, \hat{\alpha}_{\hat{\theta}}) > \gamma$, and otherwise not, where $\gamma$ is a predetermined threshold value reflecting the acceptable probability of false alarm (false alarm rate), $p_f$. The resulting detector is termed the SEAQUER detector. Since analytical expressions for $p_f$ are mathematically intractable, Monte-Carlo performance evaluation is resorted to, to determine the threshold $\gamma$. Specifically, for a given value of $\epsilon$ and a specified nonlinear search space, the test statistic is evaluated for a large number of realizations under the null hypothesis, and the $p_f$ vs. threshold curve estimated from the results (see also Section I-5) has an approximately constant false alarm rate (CFAR) with the respect to the unknown interference subspace and noise power.

I-4. The RCDAML Algorithm

In this section, the RCDAML algorithm is derived in which a pre-whitening approach for interference rejection is employed. Let $R_w$ denote the covariance matrix of the additive noise term, i.e., $$R_w = E\{w_{N\tilde{P}} w_{N\tilde{P}}^*\}. \quad (31)$$

Then, using (5), the maximum likelihood estimate of $$\underline{\theta} = [\alpha^T \bar{\theta}^T]^T, \quad (32)$$

may be found as $$\hat{\underline{\theta}} = \arg\min_{\underline{\theta}} \|r_{N\tilde{P}} - H_{\bar{\theta}}\alpha\|_{R_w}^2 \quad (33)$$

$$= \arg\min_{\underline{\theta}} \sum_{p=0}^{\tilde{P}-1} \|r_N^p - A_{\bar{\theta}}^p \alpha\|_{R_w}^2,$$

where in the last equality it has been assumed that the noise is stationary between blocks. If the sample has been adequately shielded from external RFI, and it is known that the sample under investigation does not contain any material that will produce spurious responses, then it is best to select $R_w = I$. However, as this is typically not the case in most practical scenarios, then one alternative is to use an estimate of the covariance matrix to pre-whiten any unknown noise colouring. An estimate of the covariance matrix may be formed from the last $\tilde{P}$ correlation domain blocks as $$\hat{R}_w = \frac{1}{\tilde{P}} \sum_{p=P-\tilde{P}+1}^{P} r_N^p (r_N^p)^*. \quad (34)$$

Figures 4, 5:
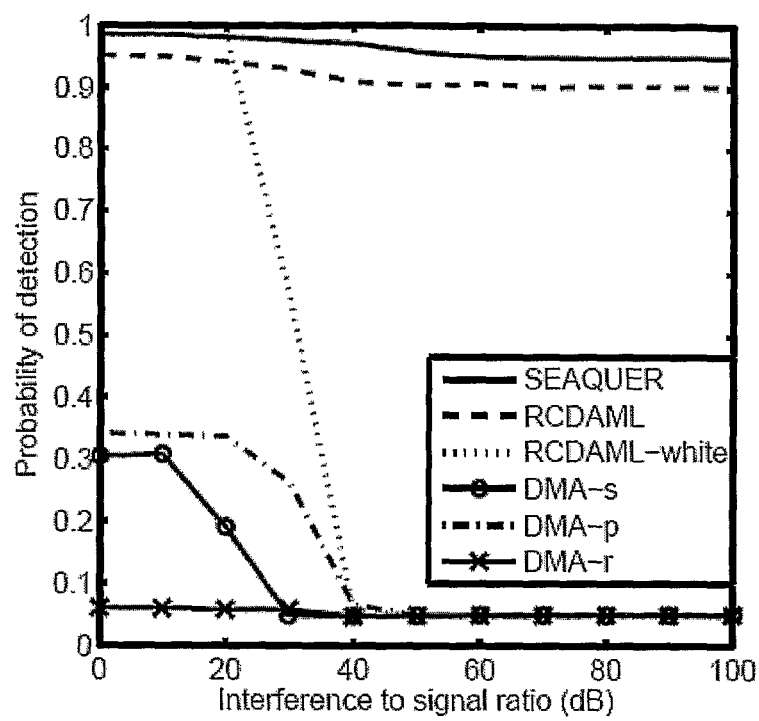
FIG. 4 is a graph showing the probability of detection as a function of the ISR, for $p_f=0.05$, using simulated data with SNR=−34 dB.
FIG. 5 is a table showing estimates of sNQR signal parameters for the d=5 lines of monoclinic TNT, for an excitation frequency of 843 kHz, in the region of 830-860 kHz.

FIG. 4 shows the probability of detection as a function of the ISR, for $p_f = 0.05$, using simulated data with SNR$= -34$ dB. Factorizing $\hat{R}_w^{-1}$ into $$\hat{R}_w^{-1} = D^* D \quad (35)$$

yields the whitening transformation D. Letting $$\check{r}_N^p = D r_N^p \quad (36)$$

$$\check{r}_{N\tilde{P}} \triangleq \left[(\check{r}_N^0)^T \ldots (\check{r}_N^{\tilde{P}-1})^T\right]^T$$

$$\check{A}_{\bar{\theta}}^p = D A_{\bar{\theta}}^p \quad (37)$$

$$\check{H}_{\bar{\theta}} \triangleq \left[(\check{A}_{\bar{\theta}}^0)^T \ldots (\check{A}_{\bar{\theta}}^{\tilde{P}-1})^T\right]^T$$

the maximum likelihood estimate of $\underline{\theta}$ is obtained as $$\hat{\underline{\theta}} = \arg\min_{\underline{\theta}} \|\check{r}_{N\tilde{P}} - \check{H}_{\bar{\theta}}\alpha\|_2^2. \quad (38)$$

Factorizing $\alpha$ as in (16), a robust estimate of $\kappa$ may be found by solving the constrained minimization $$\min_{\kappa} \left\| \check{r}_{N\check{P}} - \check{\rho}\check{H}_{\bar{\theta}}\kappa \right\|_2^2 \text{ subject to } \|\kappa - \bar{\kappa}\|_2^2 \leq \varepsilon, \quad (39)$$

where $\check{\rho}$ denotes as initial estimate of $\rho$, obtained as $\check{\rho} = \max\{|\check{H}_{\bar{\theta}}^{\dagger} \check{r}_{N\check{P}}|\}$. The minimization in (39) can be solved, via the SVD, using a method reminiscent of the one used for solving (20). Given the estimate of $\kappa$, here denoted $\check{\lambda}$, found by solving (39) and normalizing the result such that its largest magnitude equals unity, $\rho$ may be estimated as $$\check{\rho} = Re\{(\check{H}_{\bar{\theta}}\check{\kappa})^{\dagger} \check{r}_{N\check{P}}\}. \quad (40)$$

Forming $\check{\alpha} = \check{\kappa}\check{\rho}$ and substituting it into (38) yields the residual least squares error $$\check{\varphi}_{\bar{\theta}} = \|\check{r}_{N\check{P}} - \check{H}_{\bar{\theta}}\check{\alpha}_{\bar{\theta}}\|_2^2, \quad (41)$$

between the model and the observed data, where we have used the notation $\check{\alpha}_{\bar{\theta}}$ to stress the dependence of $\check{\alpha}$ on $\bar{\theta}$. Thus, similar to the SEAQUER detector, an estimate of the nonlinear parameter vector is obtained as $$\check{\theta} = \arg\min_{\bar{\theta}} \check{\varphi}_{\bar{\theta}}, \quad (42)$$

where it is stressed that at each value of $\bar{\theta}$, $\check{\alpha}_{\bar{\theta}}$ is re-estimated via (39)-(40). The test statistic is formed as an (approximate) GLRT detector, i.e., $$T(\check{r}_{N\check{P}}, \check{\alpha}_{\bar{\theta}}) = \frac{\|\check{r}_{N\check{P}}\|_2^2}{\|\check{r}_{N\check{P}} - H_{\bar{\theta}}\check{\alpha}_{\bar{\theta}}\|_2^2}, \quad (43)$$

where the signal component is deemed present if and only if $T(\check{r}_{N\check{P}}, \check{\alpha}_{\bar{\theta}}) > \gamma'$, and otherwise not, where $\gamma'$ is a predetermined threshold value reflecting the acceptable $p_f$. We term the resulting detector the RCDAML detector. Similar to the SEAQUER detector, we resort to Monte-Carlo performance evaluation to determine $\gamma'$. t to the noise power. When there is RFI, the results illustrate that the detector is approximately CFAR with the respect to the unknown interference subspace and noise power.

We remark that both the SEAQUER and RCDAML detectors require a (d+1)-dimensional search over the nonlinear parameter space. This full search may be well approximated using (d+1) one-dimensional searches, which may be iterated to further improve the fitting. This is further discussed in Paper B. Furthermore, for notational simplicity, we have here derived the SEAQUER and RCDAML detectors assuming the presence of only a single compound or polymorphic form. In previous work, we have shown (for cNQR) that when multiple polymorphs/compounds are present, it is beneficial to combine the signals from all contained components, and we have outlined an approach for dealing with multiple components of a mixture, whilst also allowing for robustness in the assumed amplitudes associated with each compound/polymorph.

FIG. 5 shows a table of estimates of sNQR signal parameters for the d=5 $v_+$ lines of monoclinic TNT, for an excitation frequency of 843 kHz, in the region of 830-860 kHz.

I-5. Numerical Examples

In this section the performance of the proposed detectors using both simulated and measured sNQR data is examined. The measured data consisted of 1000 data files, 500 with TNT present and 500 without, each taking 30 seconds to acquire. The sample, consisting of 180 g creamed monoclinic TNT, was placed inside a shielded solenoidal coil and maintained at a temperature of 295.15-296.15 K. The Quality (Q) factor of the coil and the pulse width were selected to ensure that the excitation bandwidth was sufficient to excite five $v_+$ lines of monoclinic TNT using a single excitation frequency of 843 kHz. A length P=511 stochastic excitation sequence was used, in which the phases of the RF pulses were randomized with either 0 or 180° phase shifts, using a maximum length binary sequence (MLBS). For each 30 s data file, this sequence was repeatedly applied, and the responses from each sequence summed up. Following each stochastic pulse, N=64 data points were acquired, where $D_w = 2 \times 10^{-5}$ s, yielding a time domain sequence consisting of NP=32704 samples. This time-domain signal was then cross-correlated using the fast Hadamard transform to obtain the correlation domain signal. In our experiments, Q-damping circuitry, phase cycling and the technique of composite pulses were used to suppress ringdown effects. The table of FIG. 5 summarizes the sNQR signal parameters, estimated from a high SNR signal, obtained by summing around 8 hours of data. The detectors were also compared on simulated data, with and without RFI. The simulated data without RFI, designed to mimic the measured data, was generated using (1), (2) together with the temperature shifting function constants for monoclinic TNT (see FIG. 5). For the simulations with RFI, the RFI components were added to the time-domain sNQR signal, i.e., before cross-correlation.

Figure 6:
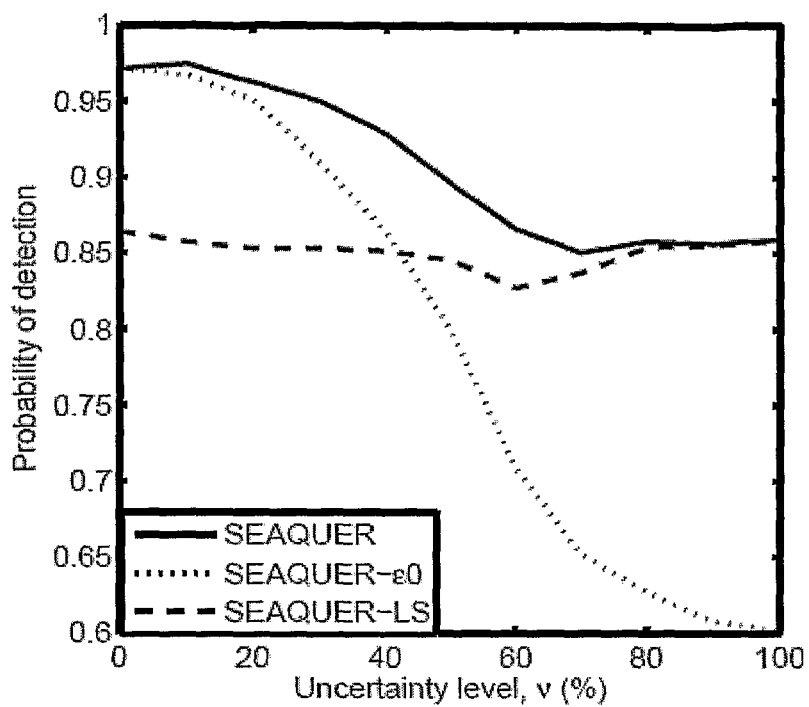
FIG. 6 is a graph showing the probability of detection as a function of the uncertainty level, for $p_f=0.1$, using simulated data with SNR=−34 dB and ISR=60 dB.

FIG. 6 shows the probability of detection as a function of the uncertainty level, for $p_f = 0.1$, using simulated data with SNR=−34 dB and ISR=60 dB.

The RFI is modelled as a set of discrete sinusoids whose frequencies and phases are uniformly distributed (over the interval $[-\pi, \pi]$), and with uniformly distributed (over the interval $[0,1]$) normalized magnitudes; here, six discrete sinusoids have been provided. It is noted that due to the chosen sampling rate, the RFI will always be within 25 kHz of the excitation frequency. The interference-to-(noise-free) NQR signal ratio (ISR) is here defined as $ISR = \sigma_1^2 \sigma_s^{-2}$, where $\sigma_1^2$ and $\sigma_s^2$ denote the power of the interference and the noise-free signal, respectively. Furthermore, the SNR is defined as $SNR = \sigma_s^2 \sigma_e^{-2}$, where cue denotes the power of the high-rank (Johnson) noise. Unless otherwise stated, in the examples using simulated data, the results were obtained from 1500 Monte-Carlo simulations.

Figure 7:
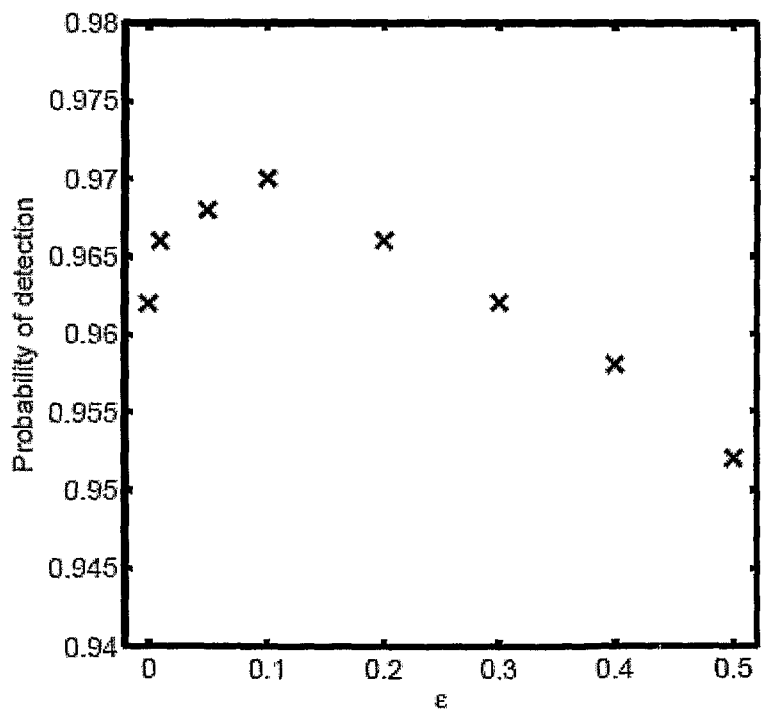
FIG. 7 is a graph showing a plot of $p_d$ vs $\epsilon$, for $p_f=0.02$, using measured data.

FIG. 7 shows a plot of $p_d$ vs $\varepsilon$, for $p_f = 0.02$, using the measured data.

Initially, the interference rejection capabilities of the algorithms is examined. As a reference, the presented detectors to the demodulation approaches (DMA), which measure the response of a single resonance frequency is also compared. The DMA-p detector is allowed perfect knowledge of the sample's temperature so that the location of the most dominant resonance is exactly known. However, for applications such as landmine detection, it is difficult to estimate the sample's temperature with more than 5 K accuracy; therefore, the $\check{R}_w = I$ is also included, corresponding to the case of no interference rejection.

It is noted that the spin-phase memory decay time for the k th resonance, here denoted $T_{2,k}^*$, is related to the associated sinusoidal damping $\beta_k$ by $T_{2,k}^* = D_w/\beta_k$. Thus, from FIG. 5, we note that $5T_{2,max}^*$ corresponds to around 410 normalized samples. Therefore, we have chosen P=5. In order to guarantee that the covariance matrix estimate in (36), used by the RCDAML detector, has full-rank, P̌=320 has been selected. The SEAQUER, RCDAML and DMA-s detectors use a search region over temperature of [290, 300] K (in 100 steps). Furthermore, the SEAQUER and RCDAML detectors use a search over each of the d sinusoidal dampings of $\beta_k$=[0.01, 0.05] (in 100 steps). In practice, the search regions could be restricted further, according to any prior knowledge concerning the sample's temperature and/or the sinusoidal dampings. FIG. 4 illustrates the probability of detection ($p_d$) as a function of the ISR, for simulated data with RFI, where the uncertainty in the complex amplitudes is selected as zero and therefore $\epsilon$=0. The figure illustrates the benefits of the proposed SEAQUER and RCDAML algorithms, especially for ISR≥30 dB, where the effect of increasing the ISR on $p_d$ is negligible. It is noted that for low ISR, the $\bar{\kappa}$, and can be obtained either by setting $\epsilon$=∞, or by using (24), instead of (29), in (30). The known and without error, and may be obtained by setting $\epsilon$=0. The standard SEAQUER algorithm selects $\epsilon$ as E{$\epsilon$}, obtained using (20), (21) and FIG. 5. We define the uncertainty parameter v, which couples the uncertainties in the phases and the magnitudes. This is further discussed in Paper B. For a given value of v, we set $$P = \pi \frac{v}{100}$$

and $\sigma_m^2$=0.0001 v. The values of E{$\epsilon$} associated with v equal to 0, 10, 20, 30, 40, 50, 60, 70, 80, 90 and 100%, were estimated using $10^6$ Monte-Carlo simulations, as 0, 0.0781, 0.2980, 0.6473, 1.1061, 1.6473, 2.2425, 2.8573, 3.4608, 4.0235 and 4.5161, respectively. FIG. 6 illustrates, for simulated data with RFI, the effect of varying the uncertainties in the complex amplitudes, indicating that the robust part of the SEAQUER detectors is unaffected by the presence of RFI.

Figure 8:
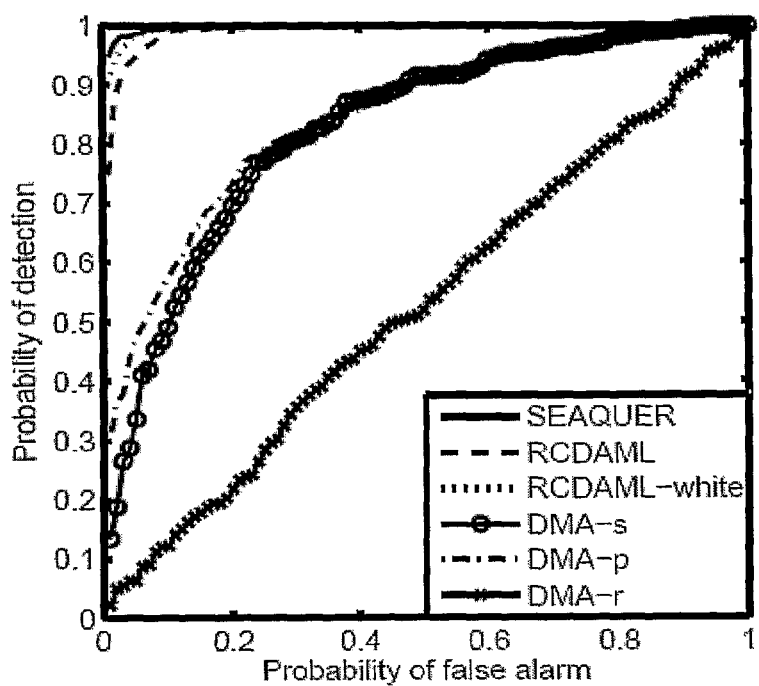
FIG. 8 is a graph showing the ROC curves for measured data, with (where applicable) $\epsilon=0.1$.

FIG. 8 shows the ROC curves for measured data, with (where applicable) s=0.1.

Figure 9:
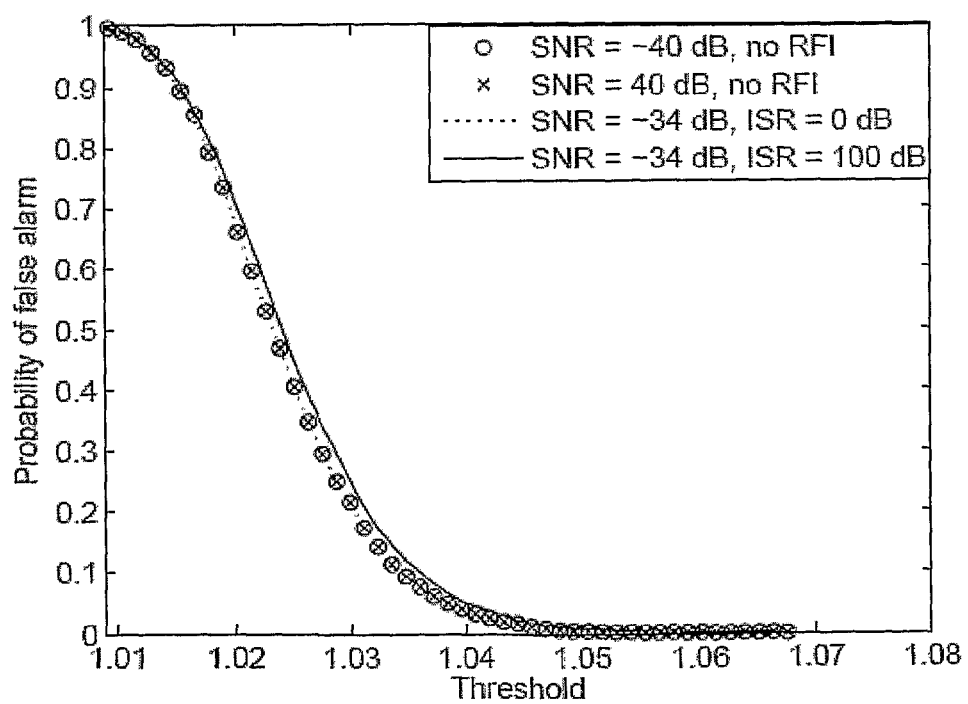
FIG. 9 is a graph showing for SEAQUER, $p_f$ vs. threshold curves for simulated data, generated using 3000 Monte-Carlo simulations.

FIG. 9 shows f SEAQUER, $p_f$ vs. threshold curves for simulated data, generated using 3000 Monte-Carlo simulations.

Figure 10:
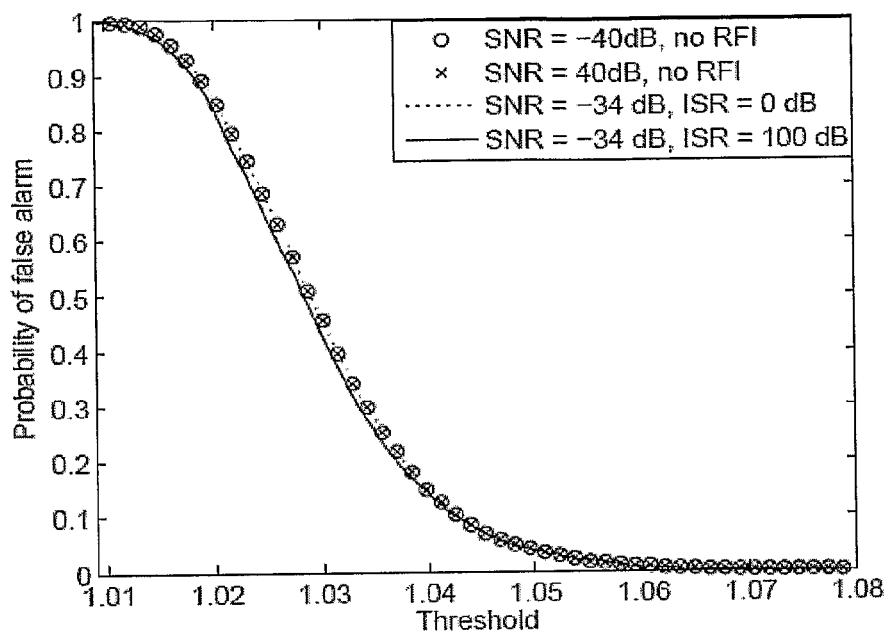
FIG. 10 is a graph showing for RCDAML, $p_f$ vs. threshold curves for simulated data, generated using 3000 Monte-Carlo simulations.

FIG. 10 shows RCDAML, $p_i$ vs. threshold curves for simulated data, generated using 3000 Monte-Carlo simulations.

For comparison, the standard SEAQUER detector is compared with two special cases, denoted the SEAQUER-LS and SEAQUER-$\epsilon$0 detectors. The SEAQUER-LS detector represents the case when no prior knowledge of the complex amplitudes is exploited, i.e. it does not exploit $\bar{\kappa}$, and can be obtained by setting $\epsilon$=∞. The SEAQUER-$\epsilon$0 detector represents the case when the relative complex amplitudes are exploited as known and without error, and may obtained by setting $\epsilon$=0.

As expected, SEAQUER-$\epsilon$0 performs well at low uncertainties when $\bar{\kappa}$ represents the observed data well. Also, as expected, for high uncertainty, it is better to use SEAQUER-LS instead of the SEAQUER-$\epsilon$0 as then $\bar{\kappa}$ is significantly in error. The standard SEAQUER algorithm is able to perform better than both the special cases as it is able to exploit $\bar{\kappa}$, but also allow for errors in it. Studies illustrate similar results for the RCDAML detector.

The measured data, obtained under laboratory conditions, is examined; hence, it can be expected that the uncertainty in the complex amplitudes to be low. FIG. 7 illustrates $p_d$ as a function of $\epsilon$ for the real data, illustrating that even under laboratory conditions, it is beneficial to allow for errors in the assumed complex amplitudes. Furthermore, as is clear from the figure, the algorithm is quite robust to the actual choice of $\epsilon$, indicating that the assumed uncertainty level does not need to be known precisely. As detection is the problem of interest, the receiver operating characteristic (ROC) curves for the SEAQUER, RCDAML are examined.

I-6. Conclusion

In this embodiment, the stochastic NQR (sNQR) data model has been introduced and the benefits of sNQR as compared to conventional NQR have been discussed. Furthermore, two detection schemes have been provided, termed SEAQUER and RCDAML, that are robust to the presence of RFI, typically observed in practical scenarios. The SEAQUER detector estimates a low-rank interference subspace, and exploits this in a matched subspace-type detector, whereas the RCDAML detector follows a pre-whitening approach, using a pre-whitening transform estimated from the data. Of the two, the SEAQUER detector is shown to have the best interference and noise rejection capability. Performance studies, using both simulated and measured sNQR data, indicate that the proposed methods show a significant performance gain as compared to existing techniques, allowing for an accurate detection even in the presence of substantial interference signals. Furthermore, numerical results illustrate that the presented detectors are CFAR with respect to the noise power, when RFI is absent, and approximately CFAR with respect to the unknown interference, when RFI is present.

Second Embodiment

Countering Radio Frequency Interference in Single Sensor Quadrupole Resonance

This embodiment describes how, in conventional spectroscopic methods, where the SOI is measured in the time domain, late SOI-free time-domain samples can be used to reduce the influence of corruptive signals.

Two examples of exploiting signal of interest free samples in conventional NQR are described. One example closely follows the algorithmic concept in SEAQUER and is therefore denoted c-SEAQUER. The second example closely follows RCDAML and is denoted RTDAML.

Note that c-SEAQUER and RTDAML are examples of two ways of exploiting the SOI-free samples to reduce the influence of corrupting signals. Persons skilled in the art will appreciate that variants of the present invention may make use of other suitable algorithms.

Nuclear Quadrupole Resonance (NQR) is a solid-state radio frequency (RF) spectroscopic technique, allowing the detection of many high explosives and narcotics. Unfortunately, the practical use of NQR is often restricted by the presence of strong RF interference (RFI). Based on stochastic NQR (sNQR), acquiring signal-of-interest free samples is described, containing only corrupting signals, and exploiting them to reduce the influence of RFI in conventional NQR (cNQR) measurements. The concept is closely related to the work in the first embodiment described above, although the algorithmic details differ sufficiently to make the extension non-trivial. Similar to the sNQR case, the presented detectors are able to substantially outperform all previously proposed cNQR detectors when RFI is present.

II-1. Introduction

Nuclear quadrupole resonance (NQR) is a solid-state radio frequency (RF) technique that can be used to detect the presence of quadrupolar nuclei, such as the $^{14}$N nucleus prevalent in many explosives and narcotics. In many NQR applications, RF interference (RFI) can be a major concern; e.g., in the detection of landmines containing TNT, the relatively weak NQR signal is significantly affected by radio transmissions in the AM radio band. Often, extra RFI mitigation needs to be employed, be it passive methods which use specially designed antennas to cancel far-field RFI, or active methods which require extra antennae to measure the background RFI. In the technique of stochastic NQR (sNQR) it has been discovered that signal-of-interest (SOI) free samples arise naturally as part of the acquisition process. We exploited these samples, deriving the SEAQUER (Subspace based EvaluAtion of QUadrupole resonance signals Exploiting Robust methods) and RCDAML (Robust Correlation Domain Approximate Maximum Likelihood) detectors, both of which are able to efficiently reduce the influence of RFI. Unlike other RFI mitigation methods, a substantial advantage of the RCDAML/SEAQUER approaches is that they do not require any additional hardware. We here concentrate on NQR signals that are obtained using conventional spin-echo techniques; however, the method is also applicable to the majority of multiple-pulse techniques. These conventional techniques are widely used in practice and are beneficial when detecting compounds with short spin-phase memory decay times, such as, e.g., orthorhombic TNT. The NQR data models used for conventional multiple-pulse NQR (cNQR) signals are significantly different to those used for sNQR, as are the acquisition processes. In sNQR, one cross-correlates the NQR response with the white exciting signal to recover the SOI or the NQR free induction decay (FID). Since only a very small amount of the correlation domain signal will contain the FID, the remainder of the signal can be considered SOI-free, i.e., SOI-free signals arise naturally in sNQR. In cNQR, the SOI is acquired in the time domain. Herein, a technique to acquire SOI-free samples, for cNQR systems, and then exploit them to reduce the influence of RFI is provided. Acquiring SOI-free samples in single-sensor cNQR has not been proposed in the literature before. Active methods exploit secondary data from extra sensors. The approach used here is fundamentally different, as only one sensor is required.

In one instance, the SOI-free samples may be used to form an estimate of a subspace spanned by the RFI components and then cancel the influence of the RFI by projecting the SOI-data and cNQR model vectors onto the space orthogonal to this subspace.

In another instance, the SOI-free samples to derive a pre-whitening transform that can be used to remove the influence of RFI is exploited.

Clearly, the performance of the proposed algorithms will depend upon how stationary the RFI is in between the 501 and SOI-free data sets and therefore it is imperative to evaluate the algorithms using realistic RFI signals. Previously the RFI has been modelled simplistically as a set of discrete sinusoids. This model is expanded to form a more realistic RFI model, so that it mimics the AM radio transmissions often present in real measurements.

The data model for cNQR signals is outlined in Section II-2. Section II-3 contains derivations for the c-SEAQUER algorithm. In Section II-4, the performances of the proposed detectors are evaluated, before conclusions are drawn in Section II-5.

II-2. Data Model

The m th echo of an echo train may be well modelled as $$z^m(t) = \sum_{k=1}^{d} \bar{C}\alpha_k e^{-\eta_k(t+m\mu)} e^{-\beta_k|t-t_{sp}|+i\omega_k(T)t} + w^m(t), \quad \text{(II-1)}$$

where $t = t_0, \ldots, t_{N-1}$ is the echo sampling time typically starting at $t_0 \neq 0$ to allow for the experimental dead time; $m = 0, \ldots, M-1$ is the echo number; $t_{sp}$ is the echo offset; $\mu$ is the echo spacing; $\alpha_k$, $\beta_k$ and $\eta_k$ denote the (complex) amplitude, the sinusoidal damping constant and echo train damping constant of the k th NQR frequency, respectively. This is further discussed in Paper B. It should be stressed that the data model for cNQR signals given in (II-1) is substantially different from the corresponding sNQR signal model. The sinusoidal damping constants and the echo damping constants, $\beta_k$ and $\eta_k$, are here modelled as unknown parameters. Furthermore, d is the known number of sinusoidal components and $\omega_k(T)$ is the known frequency shifting function (of temperature T) of the k th NQR frequency component. An approximate low order autoregressive (AR) model of known noise colouring (for instance, due to filters within the system) can be beneficially exploited and a pre-whitening filter constructed. The factor $\bar{C}$ accounts for the effect of this filter on the NQR modes. Whilst this operation will remove any known noise colouring, unknown colouring due to external RFI will still typically be present and therefore $w^m(t)$ denotes a coloured noise term.

In the following, $(\cdot)^T$, $(\cdot)^*$, $(\cdot)^\dagger$, $\|\cdot\|_2$ and $\text{Re}\{\cdot\}$ denote the transpose, the Hermitian transpose, the Moore-Penrose pseudoinverse, the two-norm and the real operator, respectively.

II-3. The c-SEAQUER Detector

Using (II-1), the in th echo may be written as $$z_N^m \triangleq [z^m(t_0) \ldots z^m(t_{N-1})]^T = A_{\bar{\theta}}^m \alpha + w_N^m \quad \text{(II-2)}$$

where $w_N^m$ is defined similar to $z_N^m$, and $$A_{\bar{\theta}}^m = (B \odot C)D^m \quad \text{(II-3)}$$

$$B = \begin{bmatrix} \zeta_1^{t_0} e^{-\beta_1|t_0-t_{sp}|} & \cdots & \zeta_d^{t_0} e^{-\beta_d|t_0-t_{sp}|} \\ \vdots & \ddots & \vdots \\ \zeta_1^{t_{N-1}} e^{-\beta_1|t_{N-1}-t_{sp}|} & \cdots & \zeta_d^{t_{N-1}} e^{-\beta_d|t_{N-1}-t_{sp}|} \end{bmatrix}$$

$$C = \begin{bmatrix} C(\lambda_1) & \cdots & C(\lambda_d) \\ \vdots & \ddots & \vdots \\ C(\lambda_1) & \cdots & C(\lambda_d) \\ C(\tilde{\lambda}_1) & \cdots & C(\tilde{\lambda}_d) \\ \vdots & \ddots & \vdots \\ C(\tilde{\lambda}_1) & \cdots & C(\tilde{\lambda}_d) \end{bmatrix}$$

$$D^m = \text{diag}\{[e^{-\eta_1 m\mu}, \ldots, e^{-\eta_d m\mu}]\}$$

$$\alpha = [\alpha_1 \ldots \alpha_d]^T$$

where $\zeta_k = e^{i\omega_k(T) - \eta_k}$, the upper block of C is $(\lfloor t_{sp} - t_0 \rfloor) \times d$, the lower block is $(N - \lfloor t_{sp} - t_o \rfloor) \times d$; the nonlinear parameter vector $\bar{\theta} = [T\beta^T \eta^T]^T$, where $\beta$ and $\eta$ denote the vectors of unknown sinusoidal and echo dampings, respectively. Using (2), the data model for the entire echo train may then be written as $$z_{NM} \triangleq [(z_N^0)^T \ldots (z_N^{M-1})^T]^T = H_{\bar{\theta}} \alpha + w_{NM} \quad \text{(II-4)}$$

where $w_{NM}$ is defined similar to $z_{NM}$, and $$H_{\bar{\theta}} = [(A_{\bar{\theta}}^0)^T \ldots (A_{\bar{\theta}}^{M-1})^T]^T \quad \text{(II-5)}$$

II-3.1. Exploitation of the Interference Subspace

Here, the coloured noise term, $w_N^m$, may be factored as $$w_N^m = S\phi^m + e_N^m, \quad \text{(II-6)}$$

with S, $\phi^m$ and $e_N^m$ denoting the basis for the interference subspace, the interference subspace weights and an additive white Gaussian noise, respectively. Thus, (2) may be rewritten as $$z_N^m = A_{\bar{\theta}}^m \alpha + S\phi^m + e_N^m. \quad (II\text{-}7)$$

Since the interference subspace will typically be unknown, it must be estimated from SOI-free data. $\check{M}$ SOI-free echoes are acquired, from which a $N \times \check{M}$ data matrix, $\check{X}$, is constructed. These SOI-free echoes are obtained after a delay of five times the longest spin-phase memory decay time after the last excitation pulse, by which time the NQR signal will have decayed to negligible levels. Excitation pulses should not continue to be applied, as this would result in having to wait for a considerably longer period (of five times the longest spin-echo decay time after the preparation pulse) for the NQR signal to decay to negligible levels. The data matrix is then factorized using the singular value decomposition (SVD), i.e., $\check{X} = \check{U}\check{\Sigma}\check{V}^*$, where $\check{\Sigma} \in R^{N \times \check{M}}$ is a diagonal matrix with the singular values arranged in non-increasing order on its main diagonal, and where $\check{U} \in C^{N \times N}$ and $\check{V} \in C^{\check{M} \times \check{M}}$ are unitary matrices containing the left and right singular vectors, respectively. The $d_{int}$ dominant left singular vectors may then be used as an estimate of the basis for the interference subspace, $\hat{S} \in C^{N \times d_{int}}$, i.e., $$\hat{S} = [\check{u}_1 \ldots \check{u}_{d_{int}}] \quad (II\text{-}8)$$

where $\check{u}_k$ denotes the k th left singular vector of $\check{X}$. Typically, the number of RFI components will be unknown. Here, minimum description length (MDL) like rule to select the rank of the interference subspace will be used, forming $$MDL(k) = N\log(\sigma_k) + k\log(N) \quad (II\text{-}9)$$

$$d_{int} = \underset{k}{\operatorname{argmin}}\{MDL(k)\},$$

where $\sigma_k$ is the k th singular value of the data matrix. Given $\hat{S}$, the maximum likelihood estimate of $\theta = [\bar{\theta}^T \alpha^T \phi^T]^T$ is given by $$\hat{\theta} = \underset{\theta}{\operatorname{argmin}} \|H_{\bar{\theta}}\alpha + G_\phi - r_{NP}\|_2^2 \quad (II\text{-}10)$$

$$= \underset{\theta}{\operatorname{argmin}} \sum_{m=0}^{M-1} \|A_{\bar{\theta}}^m \alpha + \hat{S}\phi^m - z_N^m\|_2^2, \quad (II\text{-}11)$$

where $$G_\phi = [(\hat{S}\phi^0)^T \ldots (\hat{S}\phi^{M-1})^T]^T \quad (II\text{-}12)$$

$$\phi = [(\phi^0)^T \ldots (\phi^{M-1})^T]^T \quad (II\text{-}13)$$

Minimizing (II-11) with respect to $\phi^m$ yields an estimate of $\phi^m$ as $$\hat{\phi}^m = \hat{S}^\dagger(z_N^m - A_{\bar{\theta}}^m \alpha). \quad (II\text{-}14)$$

Substituting (II-14) into (II-11) yields the compressed minimization $$\min_{\alpha,\bar{\theta}} \sum_{m=0}^{M-1} \|\Pi_{\hat{S}}^\perp [A_{\bar{\theta}}^m \alpha - z_N^m]\|_2^2, \quad (II\text{-}15)$$

where $\Pi_{\hat{S}}^\perp = I - \hat{S}\hat{S}^\dagger$.

II-3.2. Robust Complex Amplitude Estimation

To exploit the prior knowledge typically available for the complex amplitudes, $\alpha = \rho \kappa$ is first factorized, where $\rho$ is the common (real-valued) magnitude scaling due to the signal power, and $\kappa$ is the (complex) amplitude vector, normalized such that its largest magnitude equals unity. This is further discussed in Paper B. The case when the assumed (normalized) amplitude vector, here denoted $\bar{\kappa}$ is considered, as well as the actual (normalized) amplitude vector, $\kappa$, belong to an uncertainty hypersphere with radius $\sqrt{\epsilon}$, i.e., $$\|\kappa - \bar{\kappa}\|_2^2 \leq \epsilon. \quad (II\text{-}16)$$

The choice of $\epsilon$ should reflect the uncertainty in the complex amplitudes, typically obtained as a result of the experimental setup. This is further discussed in Paper B. By restricting the actual (normalized) amplitude vector to this hypersphere, an estimate of the vector best fitting the observed data can be obtained by solving the following constrained minimization $$\min_\kappa \|\rho \tilde{H}_{\bar{\theta}} \kappa - \tilde{z}_{NM}\|_2^2 \text{ subject to } \|\kappa - \bar{\kappa}\|_2^2 \leq \varepsilon, \quad (II\text{-}17)$$

where $\bar{\theta}$ is here assumed known and where $$\tilde{H}_{\bar{\theta}} = [(\Pi_{\hat{S}}^\perp A_{\bar{\theta}}^0)^T \ldots (\Pi_{\hat{S}}^\perp A_{\bar{\theta}}^{M-1})^T]^T \quad (II\text{-}18)$$

$$\tilde{z}_{NM} = [(\Pi_{\hat{S}}^\perp z_N^0)^T \ldots (\Pi_{\hat{S}}^\perp z_N^{M-1})^T]^T \quad (II\text{-}19)$$

It is Noted that an Initial Estimate of $\rho$ is Needed to Solve (17). By noting that $\rho$ is the largest magnitude in $\alpha$, an initial estimate of $\rho$ may be obtained as $\hat{\rho} = \max\{|\hat{\alpha}_{LS}|\}$ with $\max\{x\}$ denoting the maximum element in the vector x, and where $\hat{\alpha}_{LS} = \tilde{H}_{\bar{\theta}}^\dagger \tilde{z}_{NM}$ is obtained by minimizing (15) with respect to $\alpha$. This is further discussed in Paper B. Given $\hat{\kappa}$, $\rho$ may be reestimated as $\hat{\rho} = \text{Re}\{(\tilde{H}_{\bar{\theta}}\hat{\kappa})^\dagger r_{NP}\}$. Forming $\hat{\alpha} = \hat{\kappa}\hat{\rho}$ and substituting it into (15) yields the residual least squares error $$\phi_{\bar{\theta}} = \|\tilde{H}_{\bar{\theta}}\hat{\alpha}_{\bar{\theta}} - \tilde{z}_{NM}\|_2^2 \quad (II\text{-}20)$$

between the model and the observed data, the notation $\hat{\alpha}_{\bar{\theta}}$ has been used to stress the dependence of $\hat{\alpha}$ on $\bar{\theta}$. In general, $\bar{\theta}$ will be unknown and must be estimated by minimizing $\phi_{\bar{\theta}}$ over $\bar{\theta}$, using a grid search. Thus, for each value of $\bar{\theta}$, the residual error, $\phi_{\bar{\theta}}$, is evaluated using (II-17)-(II-20). The estimated value of $\bar{\theta}$ is then found as the parameter vector minimizing this error, i.e., $$\hat{\bar{\theta}} = \underset{\bar{\theta}}{\operatorname{argmin}}\ \varphi_{\bar{\theta}}. \quad (II\text{-}21)$$

The test statistic is formed as an approximate generalized likelihood ratio (GLRT) detector, i.e., $$T(\tilde{z}_{NM}, \hat{\alpha}_{\hat{\bar{\theta}}}) = \frac{\|\tilde{z}_{NM}\|_2^2}{\|\tilde{z}_{NM} - \tilde{H}_{\hat{\bar{\theta}}}\hat{\alpha}_{\hat{\bar{\theta}}}\|_2^2}, \quad (II\text{-}22)$$

where the signal component is deemed present if and only if $T(\tilde{z}_{NM}, \hat{\alpha}_{\hat{\theta}}) > \gamma$, and otherwise not, where $\gamma$ is a predetermined threshold value reflecting the acceptable probability of false alarm, $p_f$. The resulting detector is termed c-SEAQUER, where the "c" denotes conventional, to stress the difference to the sNQR version of the algorithm. c-SEAQUER requires a (2d+1)-dimensional search over the nonlinear parameter space. This full search may be well approximated using (2d+1) one-dimensional searches, which may be iterated to further improve the fitting. This is further discussed in Paper B. Furthermore, for notational simplicity, c-SEAQUER has been derived assuming the presence of only a single compound or polymorphic form. When multiple polymorphs/compounds are present, it is beneficial to combine the signals from all contained components, and an approach for dealing with multiple components of a mixture can be adopted, whilst also allowing for robustness in the assumed amplitudes associated with each compound/polymorph. This is an important matter in pharmaceutical analysis where the API (Active Pharmaceutical Ingredient) can exist in polymorphic forms which have to be identified and $^{27}$Al in clay minerals, which are mixtures of several different compounds with different quadrupole parameters but whose signals cannot be distinguished by present NMR methods.

An algorithm reminiscent of the RCDAML algorithm can also easily be derived, in which the SOI-free samples are used to form an estimate of the noise covariance matrix, from which a prewhitening transform may be obtained to reduce the effects of RFI. The results of this algorithm are here denoted the Robust Time Domain Approximate Maximum Likelihood (RTDAML) detector. Similar to SEAQUER and RCDAML, c-SEAQUER and RTDAML have a constant false alarm rate (CFAR) with respect to the additive white noise and are approximately CFAR with respect to the interference power.

Figure 11:
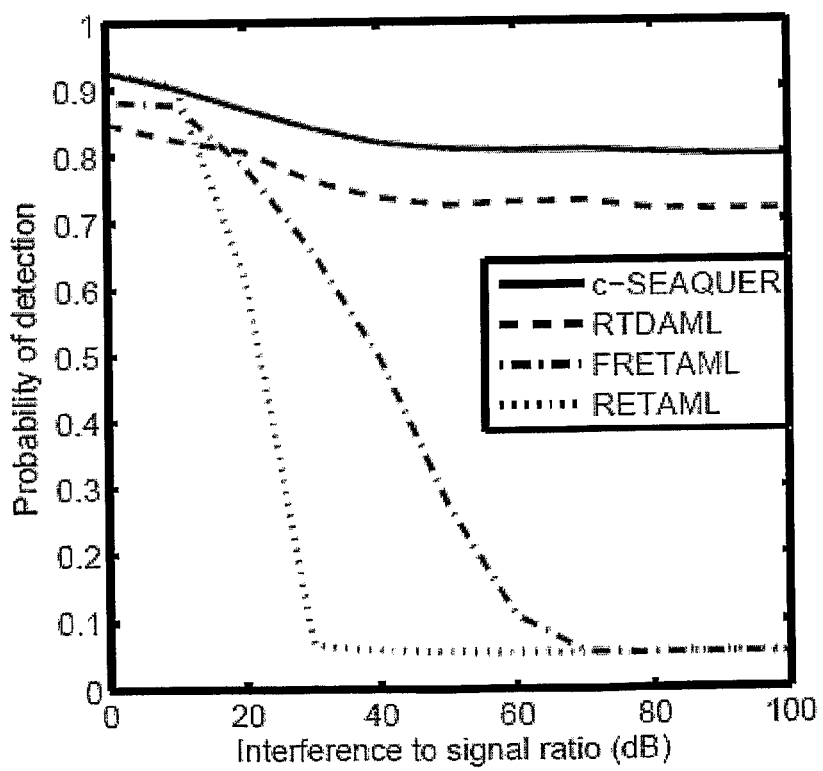
FIG. 11 is a graph showing (for the second embodiment) the probability of detection as a function of the ISR, for $p_f=0.05$, using simulated data with SNR=−27 dB.

FIG. 11 shows the probability of detection as a function of the ISR, for $p_f$=0.05, using simulated data with SNR=−27 dB.

Figure 12:
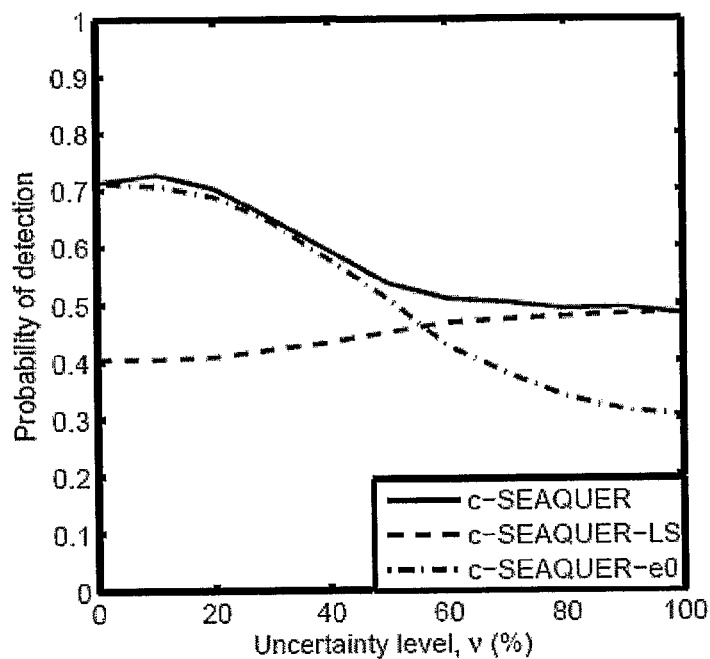
FIG. 12 is a graph showing (for the second embodiment) the probability of detection as a function of the uncertainty parameter, v, for $p_f=0.02$, using simulated data with SNR=−27 dB and ISR=60 dB.

FIG. 12 shows the probability of detection as a function of the uncertainty parameter, v, for $p_f$=0.02, using simulated data with SNR=−27 dB and ISR=60 dB.

Figure 13:
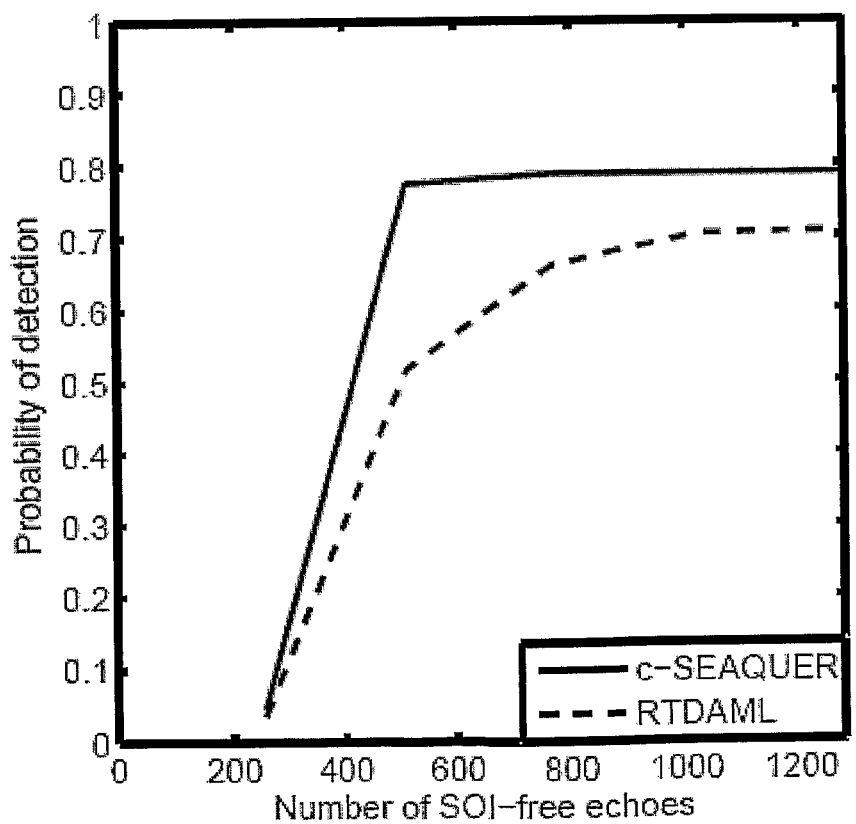
FIG. 13 is a graph showing (for the second embodiment) the probability of detection as a function of M̌, for $p_f=0.05$, using simulated data with SNR=−27 dB and ISR=60 dB.

FIG. 13 shows the probability of detection as a function of $\check{M}$, for $p_f$=0.05, using simulated data with SNR=−27 dB and ISR=60 dB.

II-4. Numerical Examples

Here, the performances of the proposed detectors are compared against current state-of-the-art detectors, namely the Robust Echo Train Approximate Maximum Likelihood (RETAML) and Frequency selective RETAML (FRETAML) algorithms, using simulated TNT data. This is further discussed in Paper B. RFI components are also added to the simulated data. Specifically, a variety of speech and audio signals are taked, sampled at 8 kHz (as for AM radio transmissions), and modulate the signals onto a carrier whose frequency is uniformly distributed over the interval [−π/4, π/4] (which corresponds to the RFI always being within 25 kHz of the excitation frequency). The resulting signal is then upsampled, according to the NQR sampling rate of 200 kHz, and added to the simulated NQR signal. The interference-to-(noise-free) NQR signal ratio (ISR) is here defined as ISR=$\sigma_1^2 \sigma_s^{-2}$, where $\sigma_1^2$ and $\sigma_s^2$ denote the power of the interference and the noise-free signal, respectively. Furthermore, the SNR is defined as SNR=$\sigma_s^2 \sigma_e^{-2}$, where $\sigma_e^2$, denotes the power of the high-rank (Johnson) noise. All results were obtained from 3000 Monte-Carlo simulations. FIG. 11 illustrates the probability of detection ($p_d$) vs the ISR, illustrating how the proposed algorithms are able to counter the RFI. The robustness to complex amplitude uncertainty is examined. Assuming a substantial interference of 60 dB, the c-SEAQUER detector is focused on, comparing it to two special cases, the c-SEAQUER-LS detector, which treats the complex amplitudes as unknown parameters, and the c-SEAQUER-ϵ0 detector, which exploits the relative complex amplitudes as known and without error. This is further discussed in Paper B. FIG. 12 shows $p_d$ vs the uncertainty parameter, v, illustrating that the robust part of c-SEAQUER is unaffected by the presence of RFI. Similar results are obtained for RTDAML. Finally, the effect of varying $\check{M}$ on the performance of the proposed algorithms is examined. FIG. 13 illustrates $p_d$ vs $\check{M}$, indicating that c-SEAQUER requires significantly lower SOI-free data support compared to RTDAML. As is clear from all of these figures, the proposed c-SEAQUER algorithm allows for a substantial improvement over the currently achievable performance of algorithms in the literature.

II-5. Conclusions

In this embodiment, a technique is provided allowing for RFI in single-sensor cNQR measurements. For the first time, we have proposed acquiring SOI-free samples, containing only corrupting signals. These samples are exploited, forming the c-SEAQUER and RTDAML detectors, both of which are able to efficiently reduce the effects of RFI. Furthermore, the performances of these algorithms on realistic cNQR signals corrupted by typical AM RFI signals are evaluated.

Third Embodiment

In another embodiment, a representation of the corrupting signals, as modelled from noise characteristics determined from the SOI-free sample, can be simply subtracted in the frequency domain from the response signal.

It will be understood that the present invention has been described above purely by way of example, and modifications of detail can be made within the scope of the invention.

Each feature disclosed in the description, and (where appropriate) the claims and drawings may be provided independently or in any appropriate combination.

Reference numerals appearing in the claims are by way of illustration only and shall have no limiting effect on the scope of the claims.

What is claimed is:

1. A method of testing for the presence of a species within a sample comprising the steps of:
    applying a resonance inducing excitation to the sample;
    detecting a resonance response signal from the sample comprising a signal-of-interest characteristic of the species and at least one corrupting signal;
    processing a first part and a second part of the response signal; and
    determining from the second part of the response signal information regarding the at least one corrupting signal with which to determine from the first part of the response signal the signal-of-interest.

2. The method according to claim 1, wherein the corrupting signal comprises a signal emanating externally to and/or not resulting from the excitation to the sample.

3. The method according to claim 1, wherein the applied excitation is a radio-frequency excitation.

4. The method according to claim 3, wherein the excitation excites in the sample at least one of:
    a nuclear quadrupole resonance;
    a nuclear magnetic resonance; or
    an electron paramagnetic resonance.

5. The method according to claim 1, wherein the corrupting signal comprises radio-frequency interference.

6. The method according to claim 1, wherein the method further comprises processing the second part of the response signal in order to obtain a model of the corrupting signal.

7. The method according to claim 6, wherein the model of the corrupting signal is used to reduce the effects of the corrupting signal in the first part of the response signal.

8. The method according to claim 1, wherein the excitation is a conventional pulse-sequence excitation.

9. The method according to claim 1, wherein the excitation is a stochastic excitation, such as a random or pseudo-random excitation.

10. The method according to claim 9, wherein the response signal is sampled by taking multiple samples between consecutive excitation pulses.

11. The method according to claim 9, wherein a signal-of-interest is obtained by cross-correlating the excitation signal with the time-domain response signal to produce a correlation-domain response signal.

12. The method according to claim 11, wherein the resulting correlation-domain signal is modelled as a gapped free-induction decay.

13. The method according to claim 11, wherein at least one algorithm is used to estimate at least one spectral parameter directly from the resulting correlation-domain signal.

14. The method according to claim 8, wherein the corrupting signal is modelled as vectors belonging to a low-rank linear interference subspace, embedded in wideband noise.

15. The method according to claim 14, wherein the second part of the response signal is used to make an estimate of the low-rank linear interference subspace.

16. The method according to claim 15, wherein vectors representing the response signal and the model of the corrupting signal are projected onto the space orthogonal to the interference subspace and thereby to reduce the influence of the corrupting signal in the part of the response signal containing the signal-of-interest, 17. The method according to claim 9, wherein the corrupting signal is modelled as vectors belonging to a low-rank linear interference subspace, embedded in wideband noise.

18. The method according to claim 17, wherein the second part of the response signal is used to make an estimate of the tow-rank linear interference subspace.

19. The method according to claim 18, wherein vectors representing the response signal and the model of the corrupting signal are projected onto the space orthogonal to the interference subspace and thereby to reduce the influence of the corrupting signal in the part of the response signal containing the signal-of-interest.

20. The method according to claim 8, wherein the corrupting signal is modelled as pure zero mean Gaussian noise.

21. The method according to claim 20, wherein the second part of the response signal is used to estimate a corresponding noise covariance matrix and to construct a transform to pre-whiten. any unknown noise colouring due to the corruptive signal and thereby to reduce the influence of the corruptive signal in the first part of the response signal containing the signal-of-interest.

22. The method according to claim 9, wherein the corrupting signal is modelled as pure zero mean Gaussian noise.

23. The method according to claim 22, wherein the second part of the response signal is used to estimate a corresponding noise covariance matrix and to construct a transform to pre-whiten any unknown noise colouring due to the corruptive signal and thereby to reduce the influence of the corruptive signal in the first part of the response signal containing the signal-of-interest.

24. The method according to claim 1, wherein the method is used to distinguish between real and counterfeit medicines.

25. The method according to claim 1, using only a single sensor.

26. The method according to claim 25, wherein the sensor is gradiometric.

27. An apparatus for testing for the presence of a species within a sample comprising:
 a transmitter, adapted to apply a resonance inducing excitation to the sample;
 a receiver, adapted to detect a resonance response signal from the sample comprising a signal-of-interest characteristic of the species and at least one corrupting signal;
 a processor, adapted to:
  process a first part and a second part of the response signal; and
  determine from the second part of the response signal information regarding the at least one corrupting signal with which to determine from the first part of the response signal the signal-of-interest.

28. The apparatus according to claim 27, wherein the corrupting signal comprises a signal emanating externally to and/or not resulting from the excitation to the sample.

29. The apparatus according to claim 27, wherein the transmitter is adapted to apply a radio-frequency excitation.

30. The apparatus according to claim 29, wherein the excitation excites in the sample at least one of:
 a nuclear quadrupole resonance;
 a nuclear magnetic resonance; or an electron paramagnetic resonance.

31. The apparatus according to claim 27, wherein the corrupting signal comprises radio-frequency interference.

32. The apparatus according to claim 27, wherein the processor is adapted to process the second part of the response signal in order to obtain a model of the corrupting signal.

33. The apparatus according to claim 32, wherein the processor is adapted to use the model of the corrupting signal to reduce the effects of the corrupting signal in the first part of the response signal.

34. The apparatus according to claim 27, wherein the transmitter is adapted to apply a conventional pulse-sequence excitation.

35. The apparatus according to claim 27, wherein the transmitter is adapted to apply a stochastic excitation, such as random or pseudo-random excitation.

36. The apparatus according to claim 35, further comprising spectrometer hardware for sampling the response signal by taking multiple samples between consecutive excitation pulses.

37. The apparatus according to claim 35, further comprising spectrometer hardware for obtaining a signal-of-interest by cross-correlating the excitation signal with the time-domain response signal to produce a correlation-domain response signal.

38. The apparatus according to claim 37, wherein the processor is adapted to model the resulting correlation-domain signal as a gapped free-induction decay.

39. The apparatus according to claim 37, wherein the processor is adapted to apply algorithms to estimate spectral parameters directly from the resulting correlation-domain signal.

40. The apparatus according to claim 34, wherein the processor is adapted to model the corrupting signal as vectors belonging to a low-rank linear interference subspace, embedded in wideband noise.

41. The apparatus according to claim 40, wherein the processor is adapted to use the second part of the response signal to make an estimate of the low-rank linear interference subspace.

42. The apparatus according to claim 41, wherein the processor is adapted to project vectors representing the response signal and the model of the corrupting signal onto the space orthogonal to the interference subspace to reduce the influence of the corrupting signal in the part of the response signal containing the signal-of-interest.

43. The apparatus according to claim 35, wherein the processor is adapted to model the corrupting signal as vectors belonging to a low-rank linear interference subspace, embedded in wideband noise.

44. The apparatus according to claim 43, wherein the processor is adapted to use the second part of the response signal to make an estimate of the low-rank linear interference subspace.

45. The apparatus according to claim 44, wherein the processor is adapted to project vectors representing the response signal and the model of the corrupting signal onto the space orthogonal to the interference subspace to reduce the influence of the corrupting signal in the part of the response signal containing the signal-of-interest.

46. The apparatus according to claim 34, wherein the processor is further adapted to model the corrupting signal as pure zero mean Gaussian noise.

47. The apparatus according to claim 36, wherein the processor is further adapted to use the second part of the response signal is to estimate the corresponding noise covariance matrix and to construct a pre-whitening transform for use in reducing the influence of the corruptive signal in the part of the response signal containing the signal-of-interest.

48. The apparatus according to claim 35, wherein the processor is further adapted to model the corrupting signal as pure zero mean Gaussian noise.

49. The apparatus according to claim 48, wherein the processor is further adapted to use the second part of the response signal is to estimate the corresponding noise covariance matrix and to construct a pre-whitening transform for use in reducing the influence of the corruptive signal in the part of the response signal containing the signal-of-interest.

50. The apparatus according to claim 27, wherein the apparatus is used to distinguish between real and counterfeit medicines.

51. The apparatus according to claim 27, comprising only a single sensor.

52. The apparatus according to claim 51, wherein the sensor is non-gradiometric.

* * * * *

UNITED STATES PATENT AND TRADEMARK OFFICE
CERTIFICATE OF CORRECTION

PATENT NO.       : 8,618,798 B2
APPLICATION NO.  : 12/935202
DATED            : December 31, 2013
INVENTOR(S)      : Somasundaram et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 727 days.

Signed and Sealed this
Twenty-second Day of September, 2015

Michelle K. Lee
*Director of the United States Patent and Trademark Office*